United States Patent
Shoham et al.

(10) Patent No.: US 11,432,876 B2
(45) Date of Patent: Sep. 6, 2022

(54) GLOBAL BALANCE USING DYNAMIC MOTION ANALYSIS

(71) Applicant: MAZOR ROBOTICS LTD., Caesarea (IL)

(72) Inventors: Moshe Shoham, Hoshaya (IL); Shlomit Steinberg, Tel Aviv (IL)

(73) Assignee: MAZOR ROBOTICS LTD., Caesarea (IL)

( * ) Notice: Subject to any disclaimer, the term of this patent is extended or adjusted under 35 U.S.C. 154(b) by 472 days.

(21) Appl. No.: 16/509,757

(22) Filed: Jul. 12, 2019

(65) Prior Publication Data

US 2020/0022758 A1 Jan. 23, 2020

Related U.S. Application Data

(63) Continuation-in-part of application No. PCT/IL2018/050052, filed on Jan. 11, 2018.
(Continued)

(51) Int. Cl.
*A61B 34/10* (2016.01)
*G16H 20/40* (2018.01)
(Continued)

(52) U.S. Cl.
CPC ............ *A61B 34/10* (2016.02); *G16H 20/40* (2018.01); *G16H 30/20* (2018.01); *A61B 5/112* (2013.01);
(Continued)

(58) Field of Classification Search
CPC .............. A61B 34/10; A61B 2034/101; A61B 2034/105; A61B 2034/107; A61B 5/1116
See application file for complete search history.

(56) References Cited

U.S. PATENT DOCUMENTS 9,149,222 B1 * 10/2015 Zets .................... A61B 5/4023
11,229,519 B2 * 1/2022 Radermacher ......... A61B 34/10
(Continued)

FOREIGN PATENT DOCUMENTS

CN 105611884 5/2016
CN 106137305 11/2016
(Continued)

OTHER PUBLICATIONS

Corresponding PCT application PCT/IL2018/050052—Search report and written opinion dated Apr. 16, 2018.
(Continued)

*Primary Examiner* — Anu Ramana
(74) *Attorney, Agent, or Firm* — Sheridan Ross P.C.

(57) ABSTRACT

An exemplary method of determining a surgical spinal correction for a subject using analysis of motion capture images of the subject, which uses the steps of obtaining pre-operative three-dimensional images of a spinal region, obtaining a pre-operative time sequenced set of images of the subject during a movement progression of said subject, calculating in a plurality of the motion capture images, alignment parameters relating to upper and lower body regions of the subject, and determining if any of the calculated alignment parameters are outside their predetermined acceptable ranges in one or more of the images, iteratively adjusting anatomical elements in three-dimensional images until all of the calculated alignment parameters are within their predetermined acceptable ranges; and adjusting spinal anatomy in the three-dimensional images according to the degree of adjustment of spinal parameters in the motion capture images to determine a surgical spinal correction.

20 Claims, 14 Drawing Sheets

Related U.S. Application Data

(60) Provisional application No. 62/487,192, filed on Apr. 19, 2017, provisional application No. 62/445,281, filed on Jan. 12, 2017.

(51) Int. Cl.

| | | |
|---|---|---|
| *G16H 30/20* | (2018.01) | |
| *A61B 90/00* | (2016.01) | |
| *A61B 5/11* | (2006.01) | |
| *A61B 5/00* | (2006.01) | |
| *A61B 17/70* | (2006.01) | |
| *A61B 17/56* | (2006.01) | |

(52) U.S. Cl.
CPC ........... *A61B 5/1127* (2013.01); *A61B 5/4566* (2013.01); *A61B 17/7074* (2013.01); *A61B 2017/564* (2013.01); *A61B 2090/061* (2016.02); *A61B 2090/067* (2016.02); *A61B 2090/374* (2016.02); *A61B 2090/3762* (2016.02)

(56) References Cited

U.S. PATENT DOCUMENTS

| | | | |
|---|---|---|---|
| 2007/0015995 | A1 | 1/2007 | Lang et al. |
| 2010/0191100 | A1 | 7/2010 | Anderson et al. |
| 2011/0213221 | A1* | 9/2011 | Roche .................. A61B 5/4504 600/301 |
| 2014/0081659 | A1 | 3/2014 | Nawana et al. |
| 2016/0045317 | A1* | 2/2016 | Lang .................... A61F 2/30942 700/98 |
| 2016/0354161 | A1* | 12/2016 | Deitz ..................... A61B 34/10 |
| 2019/0380782 | A1* | 12/2019 | McAfee ................ G16H 30/40 |
| 2020/0138518 | A1* | 5/2020 | Lang ........................ A61B 5/05 |

FOREIGN PATENT DOCUMENTS

| | | |
|---|---|---|
| JP | 2016-093497 | 5/2016 |
| WO | WO 2014/036389 | 3/2014 |
| WO | WO 2015/164421 | 10/2015 |
| WO | WO 2017/064719 | 4/2017 |

OTHER PUBLICATIONS

Aurouer, N et al. "Computerized preoperative planning for correction of sagittal deformity of the spine." Surgical and radiologic anatomy, 2009, 31.10:781.

Ferrero E et al. "Role of pelvic translation and lower-extremity compensation to maintain gravity line position in spinal deformity." J of Neurosurgery vol. 24, No. 3, pp. 436-446. Mar. 2016.

Roussouly P, Pinheiro-Franco JL. "Biomechanical analysis of the spino-pelvic organization and adaptation in pathology." Eur Spine J vol. 20 (Suppl 5), pp. S609-S618. 2011.

Wang WJ et al. "Sagittal alignment of the spine-pelvis-lower extremity axis in patients with severe knee osteoarthritis." Bone Joint Research 5, pp. 198-205. 2016.

Lee CS et al. "The effect of simulated knee flexion on sagittal spinal alignment: novel interpretation of spinopelvic alignment." Eur Spine J vol. 22, pp. 1059-1065. 2013.

Lee CS, Kang SS. "Spino-pelvic parameters in adult spinal deformities." J Korean Orthop Assoc vol. 5(1), pp. 9-29. 2016.

Cavali PTM et al. "Correlation between symptoms and sagittal alignment parameters in pAtients with lumbAr cAnAl stenosis: A case-control study." Coluna/Columna vol. 11 No. 4 São Paulo Oct./Dec. 2012.

"Biomechanics in Applications," IntechOpen, Sep. 2011, ed. Vaclav Klika, 461 pages.

Diebo et al. "Global Sagittal Angle (GSA) a Novel Parameters to Address Sagittal Alignment and Compensatory Mechanics in the Body," Euro Spine, Sep. 2-4, 2015, Copenhagen, Denmark, Abstract 482, 5 pages.

Glowacki et al. "Importance of Radiological Evaluation of Global Spinal Balance Together with Lower Limb Alignment in Planning Lumbar Spine Deformity Surgery—Illustrative Case Presentation," Polish Journal of Radiology, 2017, vol. 82, pp. 287-292.

Le Huec et al. "Equilibrium of the human body and the gravity line: the basics," European Spine Journal, Sep. 2011, vol. 20, Suppl. 5, pp. S558-S563.

Extended Search Report for European Patent Application No. 18738524.0, dated Sep. 30, 2020, 11 pages.

Official Action with English Translation for China Patent Application No. 201880012106.X, dated Mar. 9, 2022, 13 pages.

\* cited by examiner

| Parameter | Initial Contact | Opposite toe off | Heel rise | ... |
|---|---|---|---|---|
| C7TA | | | | |
| TK | | | | |
| LL | | | | |
| SVA | | | | |
| PT | | | | |
| PI | | | | |
| FOA | | | | |
| HKA | | | | |
| SSA | | | | |
| SPA | | | | |
| ... | | | | |

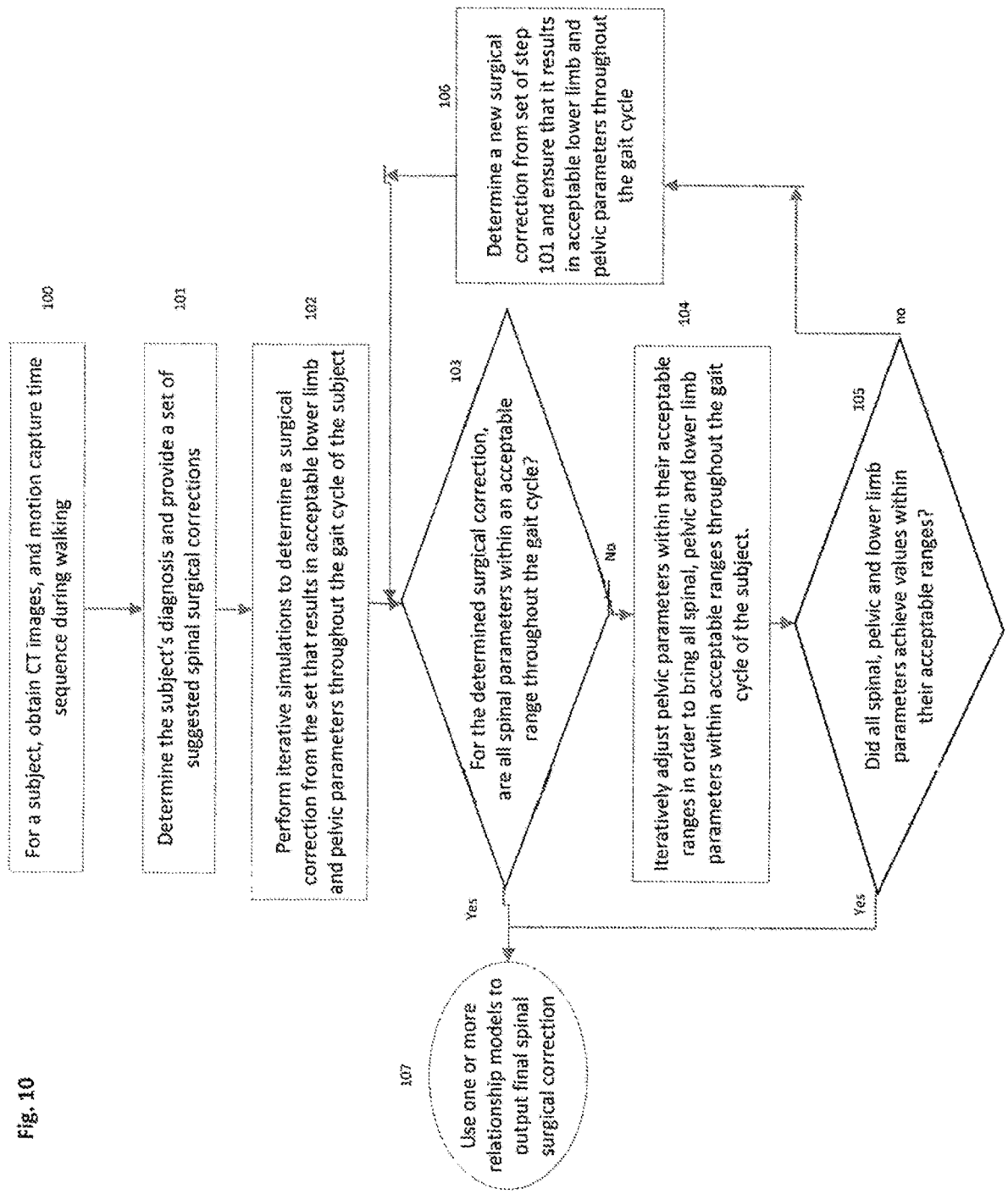

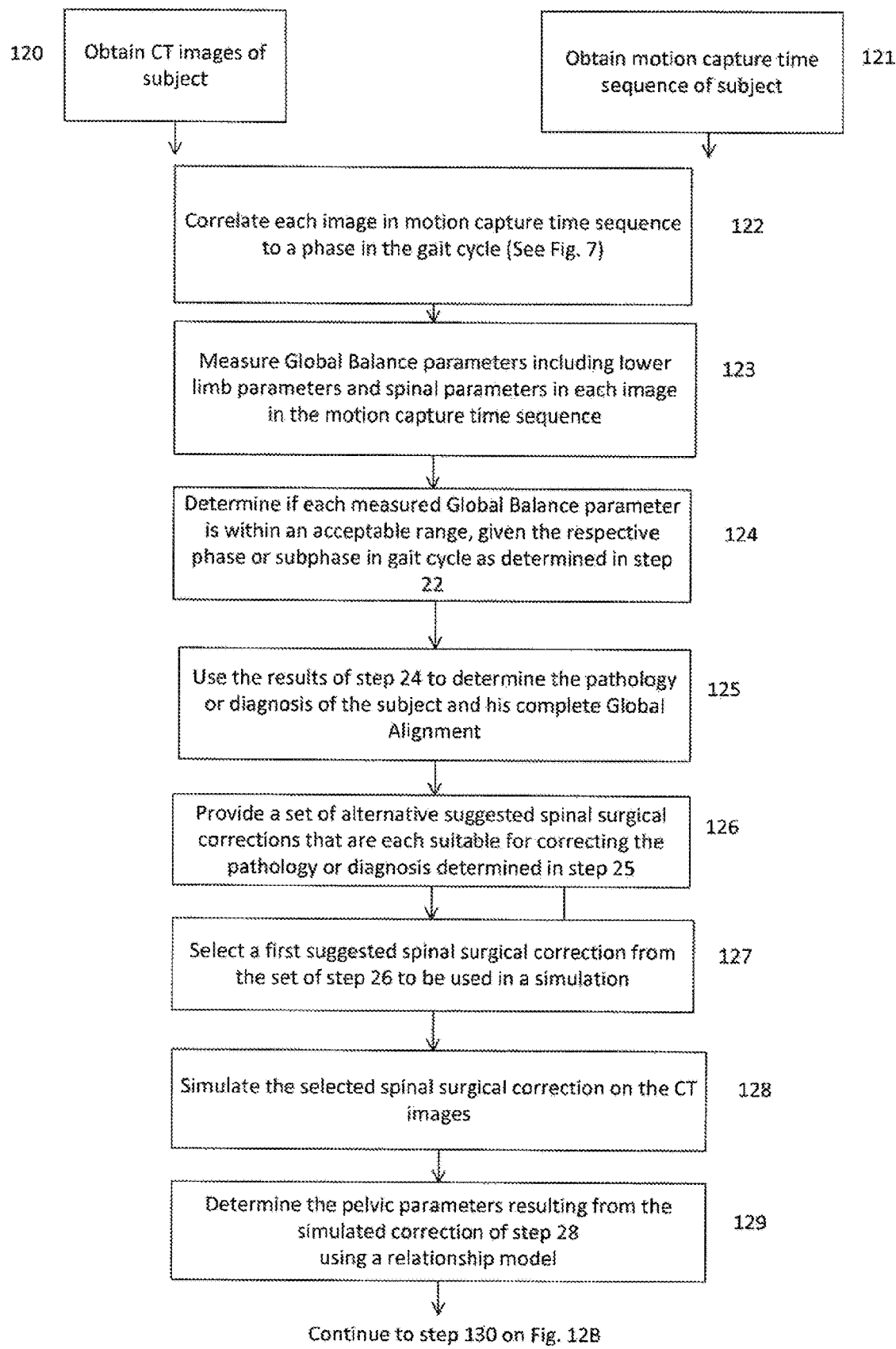

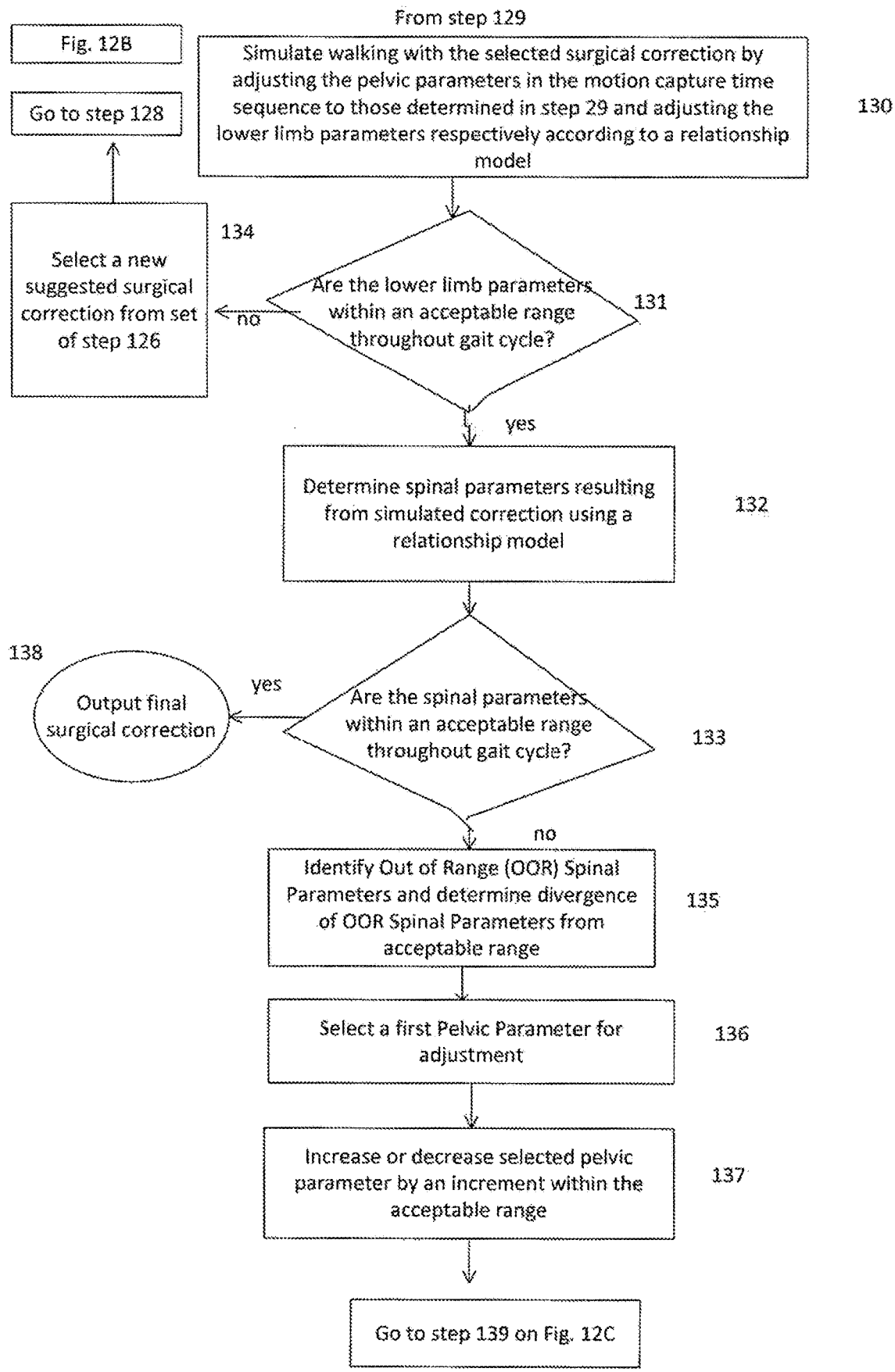

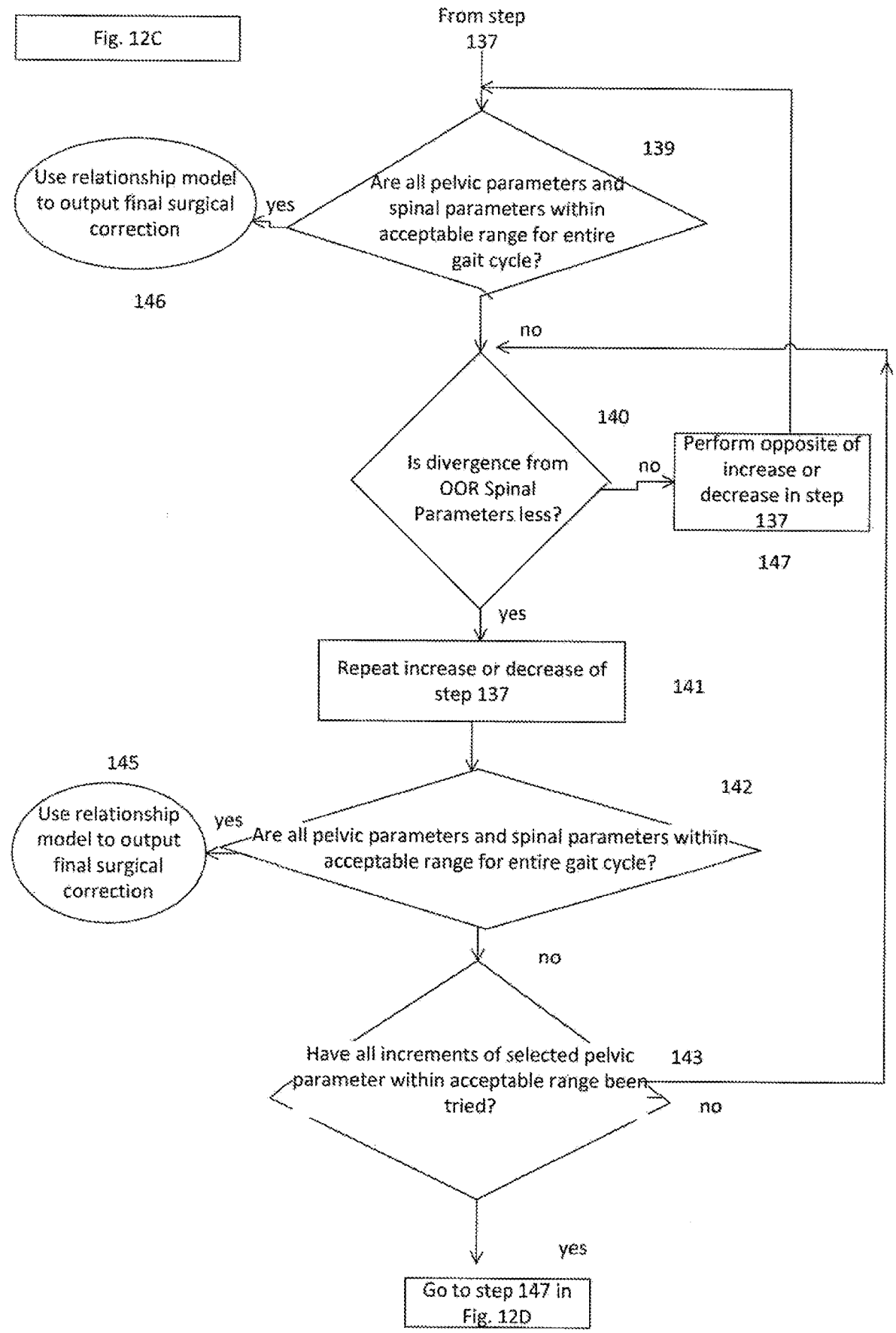

GLOBAL BALANCE USING DYNAMIC MOTION ANALYSIS

CROSS-REFERENCE TO RELATED APPLICATIONS

This application is a continuation-in-part of PCT/IL2018/050052, filed 11 Jan. 2018, which claims priority from and the benefit of U.S. provisional applications Nos. 62/487,192 and 62/445,281, filed 19 Apr. 2017 and 12 Jan. 2017 respectively. The contents of these applications are incorporated herein by reference in their entireties as is fully set forth herein.

RELEVANT FIELD

Embodiments shown in the present disclosure relate to the field of spinal surgical planning, especially using analysis of images showing motion analysis of the subject.

BACKGROUND

Planning a spinal surgical procedure to correct a spinal deformity is complex for several reasons. Any change in one or more vertebrae may affect the alignment and range of motion of the entire spine, so this "chain effect" must be taken into consideration during planning. Furthermore, since the spine is physically connected to the pelvis, and thereby to femoral heads and lower limbs, any surgical intervention on the spine also has an effect on the rest of the body and the total body balance, herein referred to as the Global Balance, of the subject, which can further affect the subject's stability when static and/or during movement such as walking. The effect of a spinal procedure on walking is of particular importance, since the role of the spine as a gait stabilizer is essential. For example, a spinal surgical procedure might change a subject's Chin-Brow-to-Vertical Angle (CBVA), or might increase or decrease knee flexion, both of these factors altering the dynamic Global Balance of the subject.

To illustrate the importance of proper spinal alignment, reference is made to FIGS. 1A to 1C, as derived from an article entitled "Biomechanical analysis of the spino-pelvic organization and adaptation in pathology" by P. Roussouly et al., published in Eur. Spine J, Vol. 20, (Supp. 5), pages S609-S618 (2011), which shows the effect of different degrees of Lumbar Lordosis on the forces affecting the Global Balance of the subject. FIGS. 1A, 1B, and 1C are schematic representations showing the effect of alignment of the spine on three forces: Gravity force (G), which may include the force of abdominal pressure, and the force (M) acting on the posterior muscles to maintain an erect position, and Contact Force (CF) on the distal lumber spine, which is the sum of G and M. The Gravity Line is further shown in each of the figures. FIG. 1A shows a normally aligned spine with acceptable force levels, FIG. 1B shows a misaligned spine, and FIG. 1C shows a severely misaligned spine. The double pointed arrow in each of the figures represents the force needed to support the corresponding body weight, resulting from the degree of Lumbar Lordosis. In FIG. 1A, which shows a normally aligned spine, this force may be decreased by abdominal pressure and stabilized by the abdominal muscles anteriorly. However, when the lumbar spine moves backward, as shown in FIGS. 1B and 1C, the posterior muscles have to work to counteract the gravity. To explain this mathematically, the more the system is unbalanced as shown by the progression from FIGS. 1A to 1C, the more the moment of G increases, and the more M has to increase to compensate for increasing CF.

The P. Roussouly article states: "The contact force (CF) on the spinal column is the addition of forward forces (gravity, abdominal pressure) and the force of the posterior spine muscles. In case of weight bearing, CF increases tremendously. In case of acute back pain, the contracture of the back muscles increases CF and the disc pressure, acting negatively on the pain. In a classical degenerative situation with loss of lordosis and progressive retroverted pelvis, the gravity line moves forward remaining at the level of the femoral heads; the distance of the anterior arrow increases and in this way CF increases." In addition to causing pain, such an unbalance and the resulting forces may cause compensatory mechanisms, such as increased knee flexion as shown in FIG. 1C, and further adversely affects the subject's movement patterns especially his gait cycle.

Therefore, a localized surgical planning approach that only takes into consideration specific vertebrae in the region of the potential surgery or a uniform, standard approach used for all subjects having different balance parameters and patterns of movement, are both likely to be inadequate. If a surgical planning method takes a localized or uniform approach, and fails to take into account either all surgically affected features of the subject, such as all of the vertebrae of the spine, the pelvis, and the lower limbs, or the way that the surgery will affect the Global Balance of the subject during dynamic movement, there may be negative outcomes. For example, if a proper balance is not achieved from a surgical procedure, the subject may experience muscle pain or use compensation mechanisms, such as knee flexion, drop foot, or limping, as his body strains to maintain an upright position during walking.

Some approaches take a comprehensive approach to planning spinal surgical procedures. For example, in PCT application published as WO 2017/064719, having common inventors with the present application, incorporated herewithin by reference in its entirety, in one exemplary embodiment, there is described a method of planning the correction of spinal deformations of a subject, using a spinal alignment optimization procedure performed by taking into consideration limitations arising from the range of motion of the vertebrae of the spine. This range is determined by analyzing quasi-static images of the subject's spine, while the subject is in positions of maximum possible bending, such as laterally, in flexion and in extension. Parameters relating to the alignment and position of the vertebrae are derived from segmentation of a three dimensional image of the spine, and it is determined whether the parameters fall within an acceptable range for the spine of the subject. If one or more parameters are not within an acceptable range, a virtual alignment optimization procedure of the spinal segments can be performed to attempt to bring the parameters within the acceptable range and to reduce the spinal deformations of the subject's spine, taking into consideration limitations arising from the range of motion of the vertebrae, and also directing the surgical corrections proposed to make optimum use of those segments of the spine in which the subject has good natural bending abilities.

The connection between a subject's ability to maintain a comfortable whole body balance with minimal energy expenditure, and the condition of the subject's spinal structure is documented in numerous articles. This relationship has been widely studied both for spinal distortions, and for spino-pelvic abnormalities, and numerous parameters have been proposed in order to attempt to achieve satisfactory balance by performing orthopedic optimizations to bring such parameters to within a predetermined desired range. One key parameter for measuring the global balance of a subject before and after spinal surgery is the Gravity Line (GL), as described in J. C. Le Huec et al, Equilibrium of the human body and the gravity line: the basics, Eur Spine J. 2011 September; 20(Suppl 5): 558-563. Published online 2011 Aug. 2. doi: 10.1007/s00586-011-1939-7. Reference is made to FIG. 2, showing the GL reference lines on a full spine representation. The GL is a vertical line passing through the center of mass of the entire body. As described in the J. C. Le Huec reference, in a healthy person, the body's GL passes very slightly behind the femoral heads, and it runs through the middle of the sacrum at a point equidistant from the two femoral heads.

Various other alignment parameters, herein referred to as Global Balance parameters, are useful for relating to the proper alignment and balance of a subject, inter alia, Chin Brow Vertical Angle (CBVA), CL (C2-C7), Ti Slope, Sagittal Vertical Axis (SVA), Pelvic Tilt Angle (PT), Pelvic Incidence-Lumbar Lordosis (PI-LL), Sacral Slope (SS), Thoracic Kyphosis (TK) or Lumbar Lordosis (LL) in the sagittal plane, and Cobb angles (a measure of spinal curvature) and Coronal Balance (CB) in the coronal plane. The term Global Balance parameters is understood to be not limited to spinal parameters, but may be any skeletal parameters that relate to a patient's full body static and dynamic balance, including, for example, pelvic and lower limb parameters.

Reference is made to FIG. 3A, which shows a subject with normal posture, and normal CBVA, and in FIG. 3B, the same subject with advanced ankylosing spondylitis, and an abnormal CBVA value of 15 degrees, such an abnormal value negatively affecting his posture alignment and gait. This image emphasizes the interconnection between the spine and the rest of the body.

If a surgical plan is not comprehensive, biomechanical disturbances may arise, for example, leading to a displacement of the trunk forwards and inducing a sagittal unbalance. If such disturbances are present in a patient preoperatively, the surgical plan must be devised to mitigate these disturbances and improve the patient's balance. Such an unbalance may necessitate excessive stresses on the anatomical structures and potentially painful muscle contractions. Three exemplary biomechanical disturbances and their evolution over time in subjects are shown in FIGS. 4A, 4B and 4C, based on the article entitled "Biomechanics in Applications", edited by Vaclav Klika, published in ISBN 978-953-307-969-1, 420 pages, Publisher: InTech, Chapters published Sep. 9, 2011 under CC BY-NC-SA 3.0 license DOI: 10.5772/1424, Edited Volume. The leftmost drawing in each of the figures represents a healthy subject in neutral position, before any disturbance.

FIG. 4A shows evolution of a subject from left to right, the subject having a lack of Lordosis (L) with a Sacral Slope (SS) value too low relative to the value of Pelvic Incidence (PI). This is a frequently observed disturbance in clinical practice for low back pain. The pelvic reaction to this loss of lordosis is generally a backward rotation (i.e. retroversion), as shown by the counterclockwise rotational arrows, achievable by extension of the hips, and by concomitant flexion of the knees and flexion of the ankles.

FIG. 4B shows evolution of a subject from left to right, the subject having an excessive Sacral Slope (SS) value reflecting a forward pelvic rotation (i.e. anteversion), as shown by the curved arrow in FIG. 4B, generally accompanied by stiff flexion of the hips, which the subject attempts to compensate for by an accentuation of the Lordosis (L). The rightmost drawing shows the subject returning to normal alignment after treatment.

FIG. 4C shows evolution of a subject from left to right, the subject having insufficient Lordosis (L) to compensate for his excessive kyphosis, with corresponding backwards pelvic rotation concomitant with low value of Sacral Slope (SS), as shown by the counterclockwise arrows in FIG. 4C, and with compensatory flexion of the hips and the knees.

Each of these three situations tends to induce an anterior translation of the gravity loads, unfavorable for the Global Balance of the subject. These three situations demonstrate compensatory mechanisms between the spinal alignment parameters, including LL, TK, and SS, and the lower limb alignment, such as hip flexion and hip extension, and therefore contribute to the Global balance of the subject.

Another important Global Balance parameter is Pelvic Incidence, as described in Biomechanics in Applications, Edited by Vaclav Klika, ISBN 978-953-307-969-1, 420 pages, Publisher: InTech, Chapters published Sep. 9, 2011 under CC BY-NC-SA 3.0 license DOI: 10.5772/1424, Edited Volume. Pelvic incidence is correlated to the ability of a subject to react to a disturbance and also to the individual risks of a loss of Lordosis. A subject with a low Pelvic Incidence value has a lower capacity to adapt to a disturbance because of low potential of Lordosis, contrary to those with a higher value of Pelvic Incidence with a great reserve of compensation. Conversely, the risk of insufficient Lordosis will be greater for the subjects with high Pelvic Incidence value, necessitating a high Lordosis value to be adapted. In case of lumbar fusion, the risk of insufficient Lordosis will be greater than in subjects with small Pelvic Incidence value, necessitating less Lordosis to compensate. Similarly, interventions not allowing an increase of lordosis (e.g. inter-somatic cages, disc prosthesis, and inter spinous blocks) should be avoided for cases with high Pelvic Incidence value, easily resulting in a disturbed sagittal balance by loss of Lordosis and a late compensation on the overlying levels which is difficult to treat. A spinal surgical planning method should analyze such individual parameters and must be integrated into the evolution of the subject. Such an approach generally allows for biomechanically efficient gravity loads on the spine and pelvis.

There has been considerable recent interest in the relationship between complete body skeletal parameters, including not only spinal and pelvic parameters, but also involving the lower extremities of the body, including the hip joint, the knees, and the ankle joints, and their connecting bone structures. Normal sagittal spine, pelvis, and lower extremity alignment is important for maintaining an ergonomic, upright standing posture and a proper walking pattern, and pathogenesis in any of these three anatomic segments may lead to poor balance, which can result in muscle strain and back pain. Furthermore, skeletal anomalies or compensation mechanisms in the pelvis and the lower extremities are often a contributory cause of lower back pain symptoms, and may result from spinal deformations. Such pelvis and lower extremity anomalies may be corrected by appropriate spinal surgical procedures, whether simple fusion, correction, or more drastic osteotomy procedures.

An article entitled "Importance of Radiological Evaluation of Global Spinal Balance Together with Lower Limb Alignment in Planning Lumbar Spine Deformity Surgery—Illustrative Case Presentation" by Glowacki et al, published in the Polish Journal of Radiology 2017; 82:287-292, stresses the importance of considering the lower limbs and pelvis in surgical planning. Regarding the lower limbs, the reference states "The assessment of global spinal balance together with lower extremity alignment should be strongly recommended." Regarding the pelvis, the reference states that the evaluation of sagittal balance is based mainly on the measurements of spinopelvic parameters, and that the pelvis is the most important link between the lower extremities and the spine, and regulates the overall body balance. However, there does not appear to be shown any method of spinal surgical planning that incorporates these relationships.

A number of new parameters have been proposed in order to quantify and characterize various conditions to define the normalcy or deviation therefrom of a skeletal structure. For example, the Global Sagittal Angle (GSA) is the angle between the line from the knee to the middle of the C7 vertebra and the line between this point and the posterior superior corner of S1 (Lafage, Virginie, "Global Sagittal Angle (GSA) A Novel Parameters to Address Sagittal Alignment and Compensatory Mechanics in the Body", NYU Hospital for Joint Diseases, Euro Spine Sep. 2-4, 2015). Other such studies that explore the relationship between the spine and lower extremities include the article entitled "Role of pelvic translation and lower extremity compensation to maintain gravity line position in spinal deformity" by E. Ferrero et al, published in Journal of Neurology: Spine, Vol. 24, No. 3, Pages 436-446 (2016), the article entitled "The effect of simulated knee flexion on sagittal spinal alignment: novel interpretation of spino-pelvic alignment" by Chung Suh Lee et al, published in European Spine Journal, Vol. 22, Pages 1059-1065 (2013), the article entitled "Spino-pelvic parameters in adult spinal deformities" by Chung Suh Lee et al, published in Journal of the Korean Orthopedic Association, Vol. 51, pages 9-29, (2016), and the above referenced review article by P. Roussouly et al. Although correlations have been discovered between spinal alignment and the pelvis and lower extremities, and parameters have been proposed that use these correlations to define proper balance and alignment of a subject, as of yet, a spinal surgical planning method has not been proposed that takes into consideration these correlations and parameters to predict the effect of different potential surgical plans on the post-surgical balance and alignment of the subject during dynamic motion. Elements that should be taken into account may include the alignment of the spine, the pelvis and the lower limbs.

Reference is made to FIG. 5, which shows a number of important Global Balance parameters. C7 transition angle (C7TA) is measured by translating the midpoint of the C7 inferior plateau (a) onto the plumb line ascending from the mid part of the S1 plateau (b). Femur Obliquity Angle (FOA) is measured as the angle between the femoral axis and the plumb line (d). Pelvic Tilt (PT) is also shown as the line between the center of the femoral head to the mid part of the S1 plateau and vertical line. In addition to the above referenced parameters, other parameters which are used in the art are to be found in articles cited in this Background Section hereinabove. Global Balance Parameters include, inter alia, GL-Heel offset, Lower limb workflow, Hip Knee Ankle (HKA), Knee flexion, Femoral offset, Neck shaft angle, femoral torsion, tibial torsion, THA-cup anteversion, cup inclinaison, femoral offset, neck shaft angle, and stem antetorsion.

As described above, the spine, pelvis, lower extremities and other skeletal features of a subject are functionally interconnected, and any surgical spinal correction has an effect on the alignment and range of motion of other skeletal features of the body, and on the global balance of the subject both in neutral position and during dynamic motion.

There therefore exists a need for a comprehensive, patient-specific method of planning the correction of spinal deformations of a subject that achieves proper alignment of essentially the entire body and global balance of the subject, both in neutral position and during dynamic motion. Such a method should result in a reduction in post-surgical back pain, surgery complications, poor posture, incidence of pathology onset, and other negative outcomes, such as may arise when only partial consideration of the subject's anatomy and balance is taken into account.

The disclosures of each of the publications mentioned in this section and in other sections of the specification, are hereby incorporated by reference, each in its entirety.

SUMMARY

Some embodiments shown in the present disclosure describe new exemplary methods for planning spinal surgical corrections, differing from those previously described by predicting the effect of a potential spinal surgery not only on spinal features, but also on the resulting positions and orientations of certain other skeletal features, and on the dynamic relationships of these features during motion of the subject. Thus in these embodiments it may be determined how a potential surgical plan will affect the pelvis and lower extremity joints, for example, the hips, knees, ankles, and feet.

Furthermore, some of the presently disclosed surgical planning methods use the novel additional steps of pre-operative dynamic motion analysis of a subject and of simulating the effects of potential spinal surgical corrections on this dynamic motion analysis, in particular on anatomical parameters that relate to balance of the subject. Such dynamic motion analysis may be performed by using motion capture technology to capture time-sequential images of a subject walking or performing other movements, and then by collecting and analyzing the data from the motion capture images for use in predictive simulations.

Some of the presently disclosed methods determine a surgical spinal correction for a subject using analysis of a time sequence of a movement progression of said subject. An exemplary method involves first obtaining pre-operative three-dimensional images such as CT or MRI images, of a spinal region of a subject, and also obtaining a pre-operative time sequenced set of images representing the subject's skeletal anatomy, preferably of his entire body, during a progression of his movement, such as a gait cycle. Alignment parameters, such as SVA, C7TA, HKA, or other Global Balance parameters, as described hereinabove, are then calculated in the motion capture images, generally in all of the images in the set, and it is determined which parameters are outside of predefined acceptable ranges (OOR) in one or more images. It is preferable to select alignment parameters relating to the entire skeleton, in both the coronal and sagittal planes so as to determine the effect of an adjustment on the entire body of the subject.

To be clear, and as one of skill in the art will appreciate upon reading the instant disclosure, the term "alignment parameter" as used throughout the description, refers to angular or distance measurements that define relationships between segments of bony anatomy of a subject, such intersegmental relationships being known to have a correlation to the subject's sagittal and/or coronal balance. Alignment parameters may relate to the spine, lower limbs, pelvis, skull, or relationships therebetween. Alignment parameters relating to the spine may be termed "spinal parameters", alignment parameters relating to lower limb anatomical elements may be termed "lower limb parameters", and alignment parameters relating to the pelvis may be termed "pelvic parameters". In calculating alignment parameters, the angular or distance measurements are performed between specific points on the bony anatomy that are known to provide useful information on intersegmental relationships of the bony anatomy. Examples of alignment parameters are C7TA, Thoracic Kyphosis, Lumbar Lordosis, Sagittal Vertical Axis, Hip Knee Ankle, Chin Brow Vertical Angle, PI-LL mismatch, Cobb angle, Pelvic obliquity, RAD, CD, AVT-T, AVT-L, Pelvic incidence (PI), Pelvic tilt (PT), Sacral slope (SS), FPA, FTA, FOA, SSA, and SPA.

According to some embodiments, a first OOR parameter is adjusted in a first motion capture image to bring the parameter within an acceptable range, by adjusting the relevant anatomical elements in the image that are associated with the chosen parameter. Other anatomical elements in the first image that have not yet been adjusted in the parameter optimization, preferably all of the other anatomical elements of the subject's body that are identifiable in the image, may then be adjusted according to known relationships between different anatomical elements, such as between the spine and the pelvis or between the spine and lower limbs, and others. Since there are such known relationships between different anatomical elements, the method may commence with optimization of spinal, pelvic or lower limb parameters. The aforementioned steps represent an optimization of the first image, representing the subject's anatomy at a single point in time of the subject's motion cycle, which then provide the basis for the adjustment of anatomy in the other motion capture images that represent different points in time of the subject's movement progression.

The anatomical elements are then adjusted in the other images of the pre-operative time sequenced set by the same degree of adjustment, for example by addition or subtraction of angles, as used in the first image. Since the pre-adjusted anatomical elements in each image were different, according to the respective phase during the movement cycle of the image, the adjustment will likewise result in a set of different images, but with each image being amended sequentially in the same general manner. The objective of the method is to obtain anatomical adjustments that result in all of the alignment parameters of interest being within their respective predetermined normal ranges in all of the images in the motion capture set, and multiple iterations of adjustments may be performed in any logical order to achieve this objective. For example, an adjustment of a selected spinal parameter may be repeatedly increased or decreased, or alternatively or additionally, a completely new anatomical parameter may be selected for adjustment. Once this objective has been achieved, selected spinal parameters of the final iteration are measured, and the degree of adjustment of these final spinal parameters from the first spinal parameters of the pre-adjusted obtained time sequenced set of images is calculated. Use can then be made of this differential to adjust the spinal anatomy, generally individual vertebrae, in the three-dimensional images, by employing predefined rules for achieving adjustment of spinal parameters through vertebral adjustment, that incorporate any of anatomical limitations, biomechanical limitations and range of motion limitations of vertebral adjustment, resulting in a final planned spinal surgical correction.

Dynamic motion analysis may be used, for example, to detect skeletal abnormalities or deformations in the pelvis or lower extremities, or to detect compensatory mechanisms. Such anomalies can often be detected, for example, by an improper gait of the subject. The gait parameters can be obtained by observing the motion of the hips, the upper leg the knee joint, and the ankle joints and feet. Examples of gait abnormalities include such features as having the stride of one leg larger than that of the opposite side, or body tilt to one side during motion. Such gait anomalies can arise, for instance, because of abnormal pelvic tilt, or pelvic rotation, or from degenerative disease of the hip or knee joints. Such dynamic motion analysis may capture compensatory mechanisms of a subject with spinal deformity, such as pelvic tilt or ankle flexion, which may advantageously be considered when evaluating and planning surgical intervention. A spinal surgical plan may be devised that reduces the need for, or negates the compensatory mechanism, which, for example, is present in the pelvis or lower extremities, and provides a healthy global alignment and balance.

Some of the disclosed methods are based on the following premises:

(i) Spinal parameters, pelvic parameters, and lower limb parameters at all points during a movement cycle, should be optimized mutually. Such dynamic movement optimization may provide an optimal surgical spinal correction that is more likely to have a positive outcome than localized approaches, such as those that only consider the effect of a surgery on a certain portion of the spine, or approaches that only consider the effect of a surgery on static or quasi-static movement.

(ii) It is possible to optimize all of these parameters mutually, since the parameters will converge as a skeleton approaches overall optimal global balance and alignment.

(iii) Spinal, pelvic and lower limb parameters are related, so any adjustment to one of these parameters may affect the other parameters.

(iv) An exemplary method of optimizing these parameters simultaneously to find the convergence mentioned in premise (ii) above, involves first optimizing lower limb parameters, then optimizing pelvic parameters according to the lower limb parameters, and then iteratively adjusting spinal or pelvic parameters until all spinal, pelvic and lower limb parameters fall within acceptable ranges throughout the movement cycle. Alternative methods may first optimize spinal parameters and then iteratively adjust lower limb or pelvic parameters. Further alternative methods may employ sophisticated multiple parameter optimization methods, as will be further discussed.

(v) The relationship of spinal parameters to lower limb parameters may be determined by the common directly related features of these two types of parameters, which are pelvic parameters. The pelvis may thus be viewed as a central link between the spine and lower limbs.

(vi) After optimization of all spinal lower limb and pelvic parameters for the movement cycle of the subject, it is possible to determine the corresponding adjustment of the spinal anatomy shown preoperatively in CT images, that would allow for this optimization, and thus to determine an optimal surgical correction for the subject that is expected to provide an acceptable or optimal movement cycle post-surgery. One or more relationship models correlating Global Balance parameters in the motion capture time sequence to Global Balance parameters obtained from CT or MRI images may be employed in this determination.

Such dynamic motion analysis not only provides a user with a comprehensive understanding of the alignment and Global Balance of the pre-operative subject during movement, but provides the foundation for an additional novel step in some embodiments of the presently disclosed methods. Using data obtained from a dynamic motion analysis in combination with data obtained from CT images, the user is able to virtually simulate visualizations of different potential spinal surgical plans, and to take into consideration the effects of each potential surgical plan on the alignment of both spinal and non-spinal features of the body of a specific subject during movement. Since the pelvis is connected to both the lower limbs and the spine pelvic parameters are used as a connecting feature in the method to correlate lower limb parameters to spinal adjustments and vice versa. For example it may be observed how virtual changes in the vertebral anatomy of the spine affect joint behavior in the pelvis and lower extremities, such as hips, knees, ankles and feet, and hence the gait of the patient. Such alignments of skeletal features or their relationships have accepted ideal quantitative values for a healthy subject, so the data from each simulation may be compared to these normal values. For example, some of the presently disclosed methods may take into consideration the correlations between the spine, pelvis rotation/translation, lower extremity motion, and the feet at different points in time during the subject's movement. In this manner, the results of analysis of the dynamics of the patient's motion during simulations can be used to propose the optimal surgical correction to the vertebrae of at least a section of the spinal region of the patient, that will improve the gait and hence the dynamic balance of the patient. Since such alignments of skeletal features or their relationships have a known correlation to the global balance of the subject, through simulations, generally iterative simulations, an optimal surgical plan can be determined that will provide the subject with good whole body balance both in neutral position and during dynamic motion.

For example, in some of the embodiments described herein, a processor-based system is able to use the anomalies in the motion of the bones of the extremities of the patient, to estimate the corrections needed in the spinal parameters of the patient, in order to compensate for the orthopedic distortions in the extremities of the patient, which generated a gait abnormality. The gait abnormality can be estimated by comparing the measured motion patterns of the markers on the patient's extremities to those of the predetermined standard gait for a healthy person, such as a standard gait for a person of similar size or build.

In an alternative method of some embodiments of the present disclosure, such corrections resulting from dynamic movement analysis may then be used in conjunction with the proposed corrections generated by a quasi-static method of spinal correction, as described in WO 2017/064719, in which the system uses X-ray images of the maximum extent of lateral bending and flexion of the patient to determine the optimum permissible surgical correction or support to be applied to the relevant vertebrae anywhere in the complete spine.

The present disclosure includes exemplary methods for spinal pathology evaluation and spinal surgical correction recommendations that are based on generally full-body data, captured during patient motion using a motion capture system. By capturing multiple time-sequential images of the subject while moving, for example, during walking or during flexion or extension, the behavior of each segment that is part of the patient's Global Balance can be assessed according to predefined Global Balance parameters. The effect of potential spinal surgical techniques may be simulated, and new motion sequence simulations may be generated showing the effects of such surgical techniques on spinal and non-spinal features (e.g. lower limbs) during dynamic movement, and the Global Balance parameters may be calculated respectively. These embodiments may achieve this by iteratively simulating corrections of Global Balance parameters, such as spinal and lower limb parameters, that fall outside an acceptable range, until all the parameters fall inside acceptable ranges.

Embodiments of the methods disclosed herein may thus achieve the following results:
1) Determine the current alignment, balance parameters and pathology of a subject, such as by entering measured values into the table, which may be performed automatically, such as that which will be shown in FIG. 8.
2) Suggest the optimal spinal surgical technique needed for achieving whole body balance during motion, and by default, whole body balance during neutral position. The surgical technique should be based on the resultant spinal parameters, the details of which may be determined by procedures described in previously mentioned WO 2017/064719.

There is thus provided in accordance with an exemplary implementation of the devices described in this disclosure, a method of determining a surgical spinal correction for a subject using analysis of a time sequence of a movement progression during motion of the subject, comprising:
(i) obtaining pre-operative three-dimensional images of a spinal region of a subject,
(ii) obtaining a pre-operative time sequenced set of images comprising spinal anatomical elements and at least one of pelvic elements or lower limb elements of the subject during a movement progression of the subject,
(iii) calculating in a plurality of the time-sequenced images, selected alignment parameters comprising at least one of a lower limb parameter or a pelvic parameter, and determining if any of the calculated alignment parameters are outside their respective predetermined acceptable ranges in one or more of the images,
(iv) on a selected pre-operative time sequenced image, adjusting at east one of lower limb or pelvic elements to bring a calculated alignment parameter that is outside of its predetermined acceptable range to within its predetermined acceptable range, and adjusting other relevant spinal anatomical elements in the image accordingly, based on known relationships between spinal and non spinal anatomical elements,
(v) adjusting spinal anatomical elements and at least one of pelvic elements or lower limb elements in other images in the pre-operative time sequenced set corresponding to the degrees of the adjustments used in step (iv),
(vi) calculating the selected alignment parameters in the other images, and if any calculated alignment parameters are not within their respective predetermined acceptable ranges, repeating steps (iii) to (v) iteratively until all of the calculated alignment parameters are within their respective predetermined acceptable ranges, and
(vii) adjusting spinal anatomy as observed in the three-dimensional images according to the degree of adjustment of the spinal anatomical elements, between those in the obtained time sequenced set of images and those in the final iteration of step (vi), to determine a surgical spinal correction.

An alternative description of the steps of the above described method may be:
(i) obtaining pre-operative three-dimensional images of a spinal region of a subject,
(ii) obtaining a pre-operative time sequenced set of images comprising anatomical elements of the subject during a movement progression of the subject,
(iii) calculating in a plurality of the images, alignment parameters relating to upper and lower body regions of the subject and determining if any of the calculated alignment parameters are outside their respective predetermined acceptable ranges in one or more of the images, (iv) on a selected pre-operative time sequenced image, adjusting anatomical elements to bring an alignment parameter that is outside of its predetermined acceptable range to within its predetermined acceptable range, and adjusting other relevant anatomical elements in the image accordingly, based on known relationships between different anatomical elements, (v) adjusting anatomical elements in other images in the pre-operative time sequenced set corresponding to the degrees of the adjustments used in step (iv), (vi) if any calculated alignment parameters are not within their respective predetermined acceptable ranges, repeating steps (iii) to (v) iteratively until all of the calculated alignment parameters are within their respective predetermined acceptable ranges, and (vii) adjusting spinal anatomy as observed in the three-dimensional images according to the degree of adjustment of spinal parameters, between those in the obtained time sequenced set of images and those in the final iteration of step (vi), to determine a surgical spinal correction.

In the above described exemplary methods, the calculated alignment parameters may comprise at least one of spinal, lower limb and pelvic parameters. In such a case, the spinal parameters may comprise at least one of cervical, thoracic, lumbar and sacral parameters.

Furthermore, the step of adjusting other relevant anatomical elements in the image based on known relationships between different anatomical elements, may reduce or eliminate amendments to anatomical elements which represent a lower limb in an image in which the lower limb has reduced weight bearing status.

According to yet a further implementation of some of the above methods described herein (including the exemplary methods described above), the predetermined acceptable ranges of the alignment parameters may be defined for each image according to the moment in time of that image during the movement progression of the subject. In all such methods, the movement progression of the subject may be either of walking or running, and the predetermined acceptable ranges may be defined according to phases in the gait cycle. Furthermore, the movement progression of the subject may be spinal extension, flexion or rotation.

In any embodiments of the above described methods, the step of adjusting spinal anatomy in the three-dimensional images according to the degree of adjustment of spinal parameters, may further be performed according to at least one of anatomical limitations, biomechanical limitations, and range of motion limitations of the subject.

Additionally, any of the previous described methods may further comprise determining a diagnosis of the subject based on the calculated alignment parameters. These alignment parameters may be derived from any type of relations between anatomical elements which are at least one of angular and distance measurements. These alignment parameters may also comprise at least one of C7TA, Thoracic Kyphosis, Lumbar Lordosis, Sagittal Vertical Axis, Hip Knee Ankle, Chin Brow Vertical Angle, PI-LL mismatch, Cobb angle, Pelvic obliquity, RAD, CD, AVT-T, AVT-L, Pelvic incidence (PI), Pelvic tilt (PT), Sacral slope (SS), FPA, FTA FOA, SSA, and SPA. Furthermore, the predetermined acceptable ranges of the alignment parameters may further be defined according to the body type of the subject.

In further implementations of the above described methods, the pre-operative time sequenced set of images may be obtained using a motion capture time sequence camera that images markers on the subject indicating the anatomic elements.

Additionally, the above mentioned step (iv) of adjusting other relevant anatomic elements in the image may be performed using a database comprising known relationships between any of the spine, pelvis and lower limbs.

In the above described methods, in which the calculated alignment parameters comprise at least one of spinal, lower limb, and pelvic parameters, above mentioned steps (iv) to (vi) may comprise first adjusting pelvic alignment parameters until they are all within normal ranges, and subsequently adjusting spinal alignment parameters. Alternatively, steps (iv) to (vi) may comprise first adjusting spinal alignment parameters until they are all within normal ranges, and subsequently adjusting pelvic alignment parameters. In either of these cases, step (iv) may further comprise adjusting pelvic alignment parameters to bring lower limb alignment parameters within normal ranges. In all of these cases, adjusting other relevant anatomic elements in the image in step (iv) may be performed to comply with the previously adjusted anatomical elements.

Finally, in any of the embodiments of the above described methods, the three-dimensional images may be any one of CT images, X ray images, or MRI images, and they may comprise a set of two-dimensional images of the subject.

To be clear, and as one of skill in the art will appreciate upon reading the instant disclosure, the term system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components, such as optical, magnetic, or solid state drives, that provide the described functionality; or a combination of some or all of the above, such as in a system-on-chip. The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this disclosure may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

BRIEF DESCRIPTION OF DRAWINGS

Embodiments of the present disclosure will be understood and appreciated more fully from the following detailed description, taken in conjunction with the drawings in which:

FIG. 1A shows a normally aligned spine, FIG. 1B shows a misaligned spine, and FIG. 1C shows a severely misaligned spine.

FIG. 10 is an exemplary overview flowchart of an alternative method of planning a spinal surgical correction using iterative pelvic parameter adjustments in dynamic motion image(s).

FIGS. 12A, 12B, 12C and 12D show an exemplary detailed flowchart of the method of FIG. 10.

DETAILED DESCRIPTION

Figure 6:
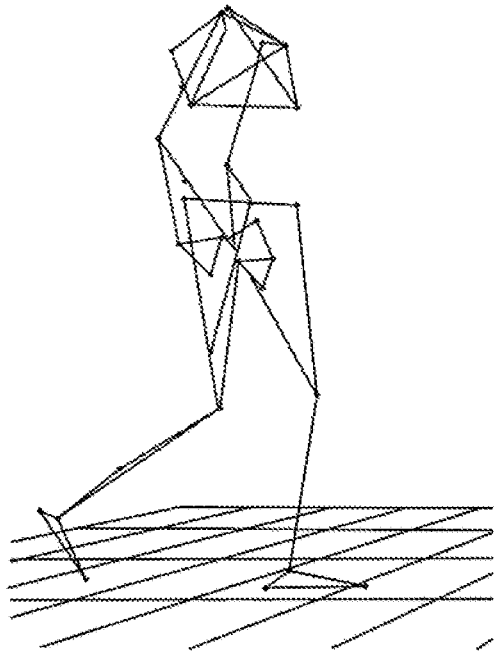
FIG. 6 is an exemplary motion capture time sequence image of a subject during walking.

Reference is made to FIG. 6, showing an exemplary motion capture image taken of a subject during walking. Such systems generally generate video sequences of the patient while moving and use image processing of video sequences by analyzing the motion of markers attached at numerous locations on the patient's body usually including his extremities. From the motion data in these videos, the system software is able to generate simulations of how each of the skeletal features of the patient, such as the spine, pelvis and the bones of the lower extremities, change position during motion of the patient. The drawing is a three-dimensional representation, and the lines shown in the drawing represent connection lines between markers on anatomical points of the subject. The cervical, thoracic and lumbar spine regions should preferably be identified for optimal Global Balance parameter analysis and optimization.

To ensure that the maximum amount of data may be collected, a plurality of cameras may be positioned at multiple locations around the subject, and images may be collected at a fast rate, for example 240 frames per second, or more. Images may be obtained showing the position of the subject's attached markers, corresponding to his specific skeletal features, at specific points in time. Such positions may be relative to a fixed point on the image or to the position of other skeletal features. Alternatively, data related to the subject's movement may be obtained over a longer period of time, for example over a day or a week, by attaching wearable sensors to the subject and transmitting the collected data to a computer system, such as a mobile phone. Such an alternative may be used when it is desirable to obtain a larger body of data related to the extremities of the subject's movement for determination of whether these extremities are within a normal or optimal range, such as his maximum extension or flexion, since throughout this longer time period the subject will reach maximum extension or flexion multiple times.

The movement of the subject in the images may be compared to the movement of a healthy person or to an optimal model such as that having parameters within acceptable ranges. This step may be performed by correlating each of the images to a phase during a movement cycle, for example, a gait cycle such as will be described in accordance with FIG. 7, with each phase having predefined normal Global Balance parameters. The Global Balance parameters may then be measured in each image and compared to the normal or acceptable range, given the respective phase in the gait cycle.

Figures 7, 8:
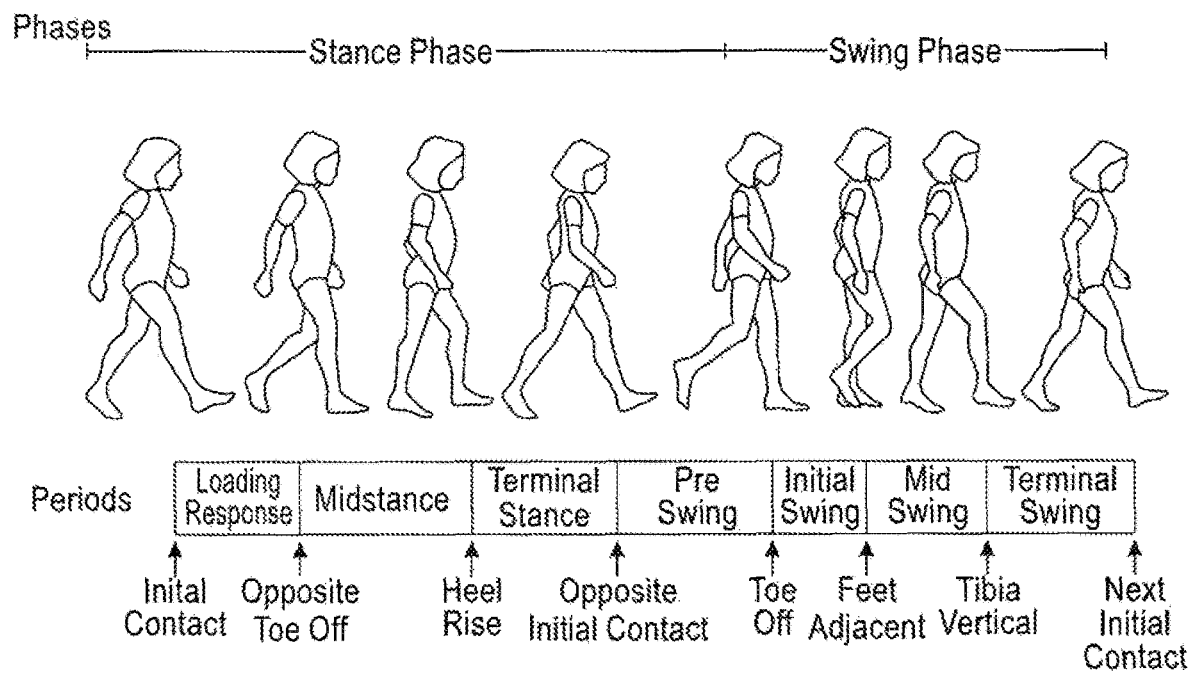
FIG. 7 is a schematic exemplary drawing showing phases during a gait cycle of a subject.
FIG. 8 is an exemplary table showing multiple lower limb, spinal and pelvic Global Balance parameters and their respective acceptable ranges for the phases during the gait cycle.

Reference is now made to FIG. 7, showing exemplary phases during a gait cycle of a subject. It is clear from this drawing that the parameters will be different at each phase of the cycle even for a healthy person. For example, for the Initial Contact phase, it may be known what the acceptable range is for each the selected parameters of C7TA, TK, LL, and SVA, and at the end of the initial swing phase, the subject exhibits a high degree of knee flexion in her right leg. Alternatively, Global Balance Parameters may be determined during subphases of these phases. Additionally or alternatively to gait cycle analysis, different types of movement and their respective phases may be used, for example, if spinal flexion is being analyzed, the first phase may be 20% flexion, the second phase may be 30% flexion, the third phase may be 40% flexion, and so on until full flexion is achieved. Other possible types of movement for analysis include, inter alia, running, walking backwards, walking sideways, walking up stairs, spinal extension, spinal rotation or twisting, lateral spinal bending, and jumping.

FIG. 8 shows an exemplary table used for entering data related to measured Global Balance parameters at each phase in the gait cycle. FIG. 8 shows the large array of data that may be generated in such a motion capture sequence. Each value entered may then be compared to an acceptable range for that cell.

Figure 9A:
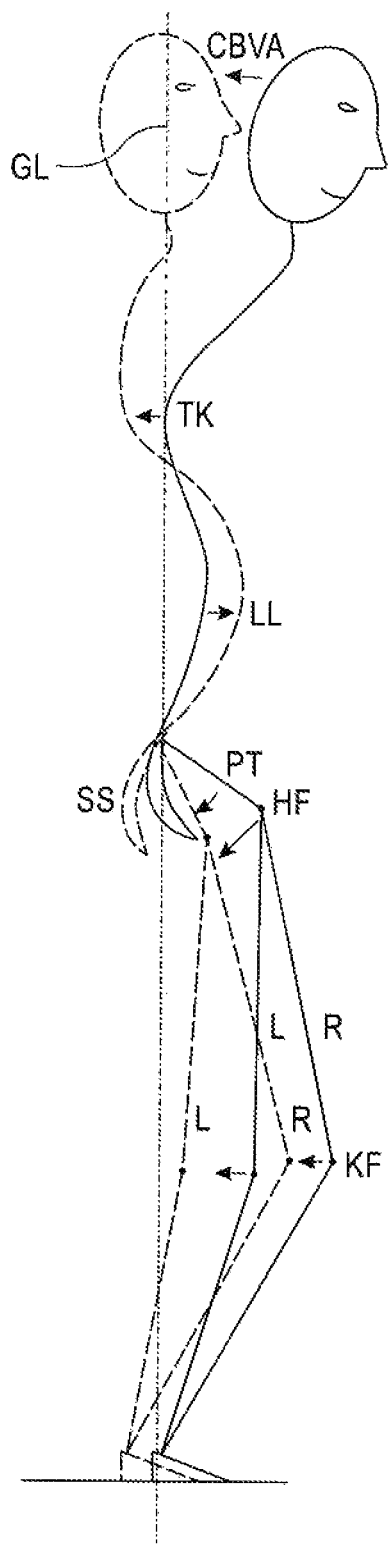
FIGS. 9A and 9B illustrate schematically an exemplary manner in which parameter adjustments and anatomical feature adjustments may be performed on motion capture images to bring Out of Range (OOR) Global Balance parameter(s) to within acceptable ranges.
Figure 9B:
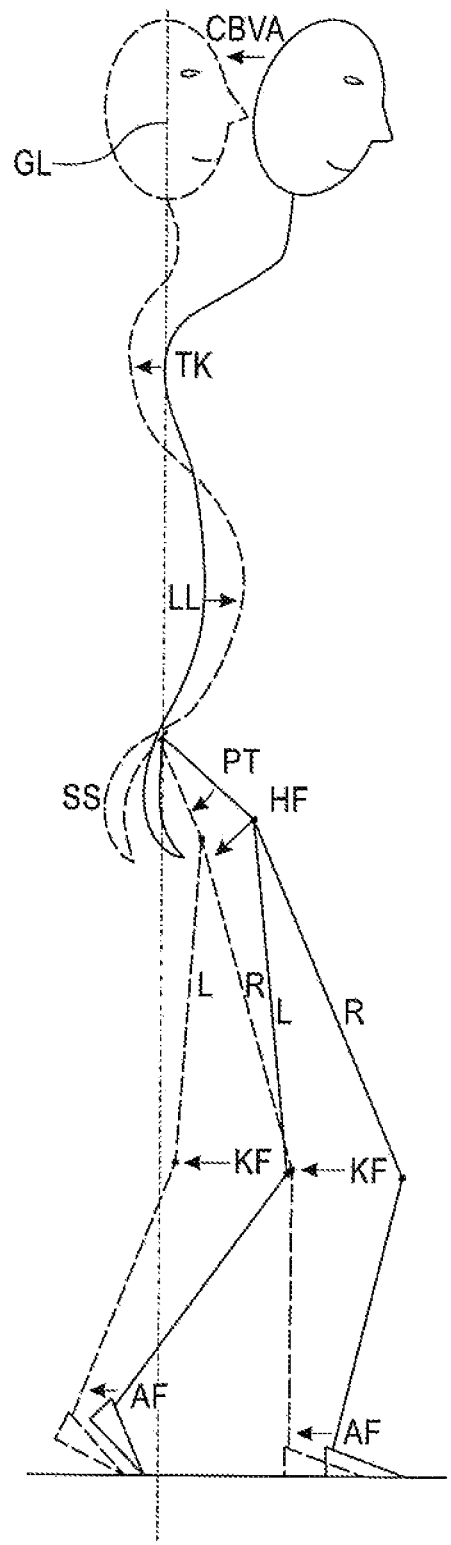

Reference is now made to FIGS. 9A and 9B, which illustrate schematically an exemplary manner in which parameter adjustments may be performed on motion capture images. In FIGS. 9A and 9B, two exemplary images from a motion capture time sequence are shown to illustrate the method, although the method would generally use all of the images in a dynamic movement or motion progression set. FIG. 9A shows an exemplary representation of a subject's skeleton in the "heel rise" phase position of a walking cycle, as derived from a motion capture time sequence of images, and FIG. 9B shows an exemplary representation of a subject's skeleton in the "opposite toe off" phase position of a walking cycle. These terms are part of an exemplary nomenclature of the art, used in describing the walking gait of a subject, though there are other sets of nomenclatures used for defining phases in a gait cycle, and these may likewise be used. The subject shown in the example of FIGS. 9A and 9B suffers from lack of Lumbar Lordosis (LL) with a Sacral Slope (SS) value too low relative to the value of Pelvic Incidence (PI), and as a result, is expected to suffer from low back pain. It is also noted that the subject in FIGS. 9A and 9B exhibits compensation mechanisms, including, inter olio, increased knee flexion, increased ankle flexion, and pelvic retroversion, which negatively affect his balance and walking. The full lines represent the pre-adjustment positions of his anatomical features, and the dotted lines represent the adjustment proposed to attempt to restore acceptable Global Balance spinal, pelvic and lower limb parameter values for his entire skeleton in both of the phases shown in the drawings.

As shown in FIG. 9A, an exemplary adjustment of anatomical features identified in the image that represent the subject's lumbar spine is first made to increase the subject's Lumbar Lordosis (LL) by a selected increment that will result in a new LL value within the acceptable range. Subsequently, other anatomical features identified in the image are adjusted according to expected corresponding anatomical parameters resulting from the LL adjustment, such as Thoracic Kyphosis (TK), CBVA (Chin-brow-to-vertical angle), Pelvic Tilt (PT), Sacral Slope (SS), hip extension or flexion, and knee flexion. These adjustments may be based on known expected relationships between anatomical elements and their respective parameters, and also based on known expected relationships between different alignment parameters, for example between spinal parameters and pelvic parameters. For example, in FIG. 9A, as a consequence of the LL adjustment, the subject's Pelvic Tilt will be rotated forwards (i.e. anteversion), as shown by the curved arrow. Likewise, his Thoracic Kyphosis (TK) will be increased and his CBVA decreased to straighten his upper spine and head. Likewise, the subject's knee and ankle flexion will be decreased in both legs, such as by adjusting anatomical features identified in the image as representing his tibia and femur to be moved closer to his Gravity Line (GL), and his SS will be increased. The essentially full skeletal anatomy of the subject has thus been adjusted on a first image of the motion capture time sequence based on optimization of his LL.

Reference is made to FIG. 9B, schematically showing the same subject at a different phase during the gait cycle, in this drawing shown as being the opposite toe-off phase. The same parameters, LL, TK, SS, PT, and CBVA, are then adjusted in this second image by making adjustments to the anatomical elements on which these parameters depend. The degree of adjustment of the parameters for the spine and pelvis is generally performed using the same increment, such as increase by an incremental angle or incremental distance, as was adjusted in the first image. The degree of adjustment of the parameters related to each of the lower limbs, such as knee and ankle flexion, may be performed according to the respective degree of weight bearing on each lower limb. It is to be understood that the adjustment to be made to the anatomical elements of the lower limbs, such as those related to the above mentioned knee flexion and ankle flexion, may be different for the subject's two legs, since, depending on stance, there will be images in which there is reduced or zero weight bearing forces on one leg, in which case the need for element adjustment of the non-weight bearing leg may be reduced or eliminated for that moment of the subject's gait, while to the other weight bearing leg, the full adjustment determined in the first image must be applied.

Reference is made to FIG. 10, showing an overview of one exemplary method for determining an optimal spinal surgical correction using iterative pelvic parameter adjustments in dynamic motion capture images.

In step 100, pre-operative three-dimensional images, such as CT images, and pre-operative motion capture time sequences of a subject during walking are obtained.

In step 101, the subject's pathology or diagnosis may be determined from the motion capture and three-dimensional images, and a set of suggested spinal surgical corrections is provided based on the determined pathology or diagnosis. From this set of suggested surgical corrections, an optimal spinal surgical correction will ultimately be chosen based on the corresponding determined anatomical parameters measured during simulated walking.

In step 102, iterative simulations are performed to determine a surgical correction from the set that results in acceptable selected lower limb parameters and selected pelvic parameters throughout the gait cycle of the subject. This step may be performed, for example, by measuring the pelvic parameters (e.g. PT, PI) resulting from a certain suggested spinal surgical correction in each of the motion capture images, then adjusting one or more pelvic parameters that were not within acceptable ranges by adjusting anatomical features representing the pelvis in the images. Then, a relationship model relating lower limb parameters (e.g. HKA) to pelvic parameters may be used to adjust the lower limb parameters respectively in the motion capture images to determine if the lower limb parameters are within an acceptable range throughout the gait cycle.

For a spinal surgical correction which has been deemed acceptable for the lower limb and pelvic parameters, it is then determined, in step 103, if selected spinal parameters are within an acceptable range throughout the gait cycle. If the spinal parameters are within an acceptable range throughout the gait cycle, one or more selected relationship models relating any of spinal, pelvic and lower limb parameters to positions of spinal features in the three-dimensional images may be used to output a final spinal surgical correction in step 107. For example, the methods described in PCT Application published as WO 2017/064719 may be used. If the spinal parameters are not within an acceptable range throughout the entire gait cycle, one or more pelvic parameters are adjusted iteratively within their acceptable ranges in step 104 in order to bring all spinal, pelvic, and lower limb parameters within acceptable ranges throughout the gait cycle of the subject. The iterative adjustments in the motion capture images as described above may be performed in accordance with the method of FIGS. 9A and 9B, for example.

In step 105, it is determined if all spinal, pelvic and lower limb parameters achieved values within their acceptable ranges. If any of the parameters are not within acceptable range, in step 106 a new surgical correction is selected from the set of step 101 and it is ensured that it results in acceptable lower limb and pelvic parameters throughout the gait cycle, and then the method returns to step 103 to determine if the spinal parameters are within an acceptable range throughout the entire gait cycle.

Once a surgical correction has been determined for which all spinal, lower limb and pelvic parameters are within their respective acceptable ranges throughout the gait cycle, then in step 107, relevant models that relate spinal, pelvic and lower limb anatomical parameters at all phases throughout a simulated gait cycle to simulated surgical spinal corrections on three-dimensional images of the spine are selected. From these models it is possible to determine a corresponding surgical correction for the previously optimized parameters. Such a model may, for example, be able to determine how, for certain lower limb and pelvic parameters in a motion capture sequence, spinal anatomy would need to be adjusted in the three-dimensional images to obtain such parameters, that being the desired spinal surgical correction.

Figure 11:
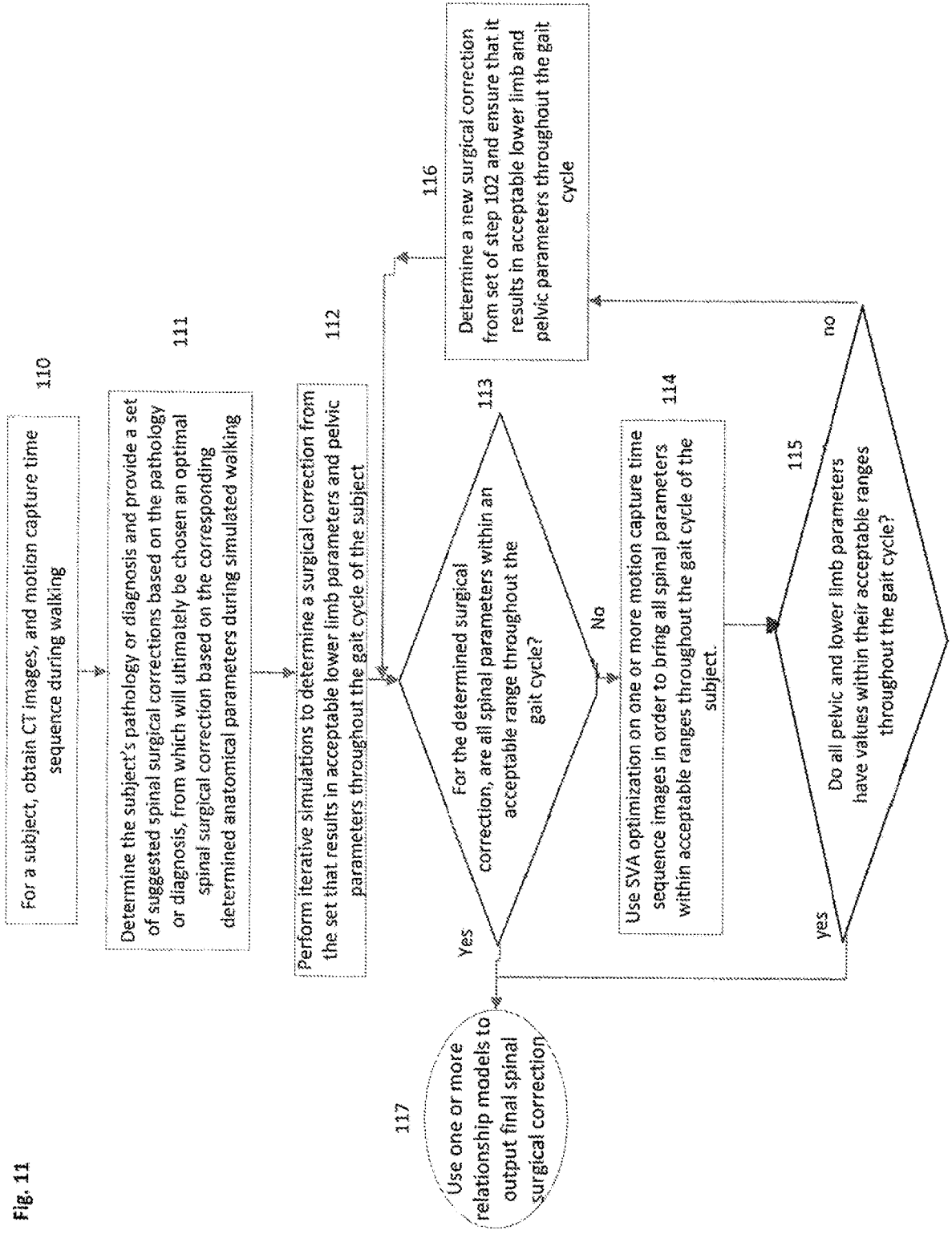
FIG. 11 is an exemplary overview flowchart of an alternative method of planning a spinal surgical correction using iterative spinal parameter adjustments in dynamic motion image(s).
Figure 12D:
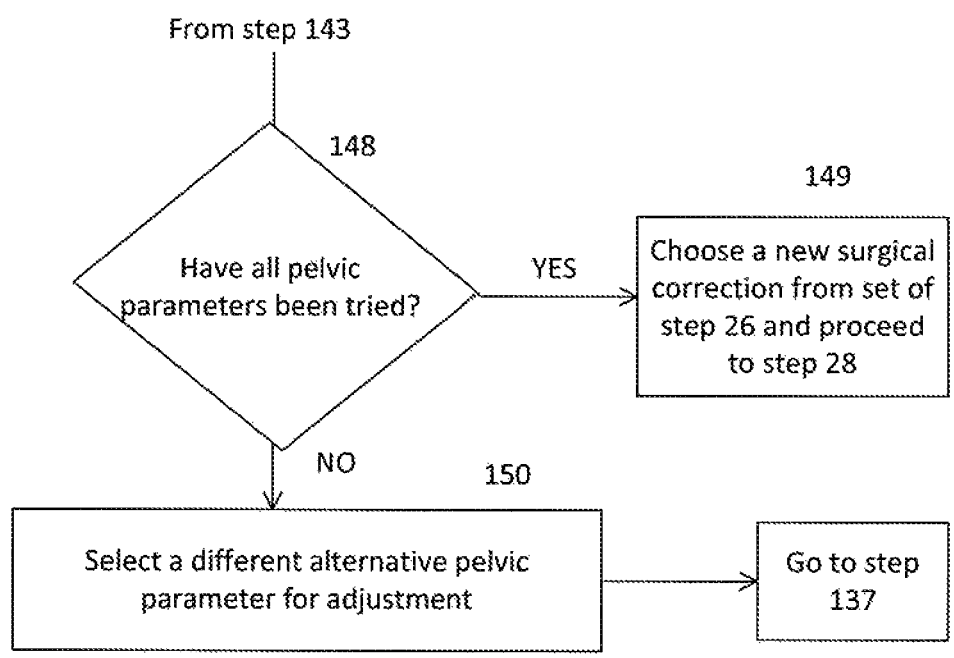

FIG. 11 shows an overview of an alternative exemplary method of determining an optimal spinal surgical correction using iterative spinal parameter adjustments in dynamic motion capture images. Instead of using iterative adjustments of pelvic parameters to bring Out of Range (OOR) spinal parameters within range as described in accordance with FIG. 10, this method uses iterative adjustments of spinal parameters to accomplish this goal.

In step 110, pre-operative three-dimensional images, and pre-operative motion capture time sequences of a subject are obtained during walking.

In step 111, the subject's pathology or diagnosis may be determined from the motion capture and three-dimensional images, and a set of suggested spinal surgical corrections is provided based on the determined pathology or diagnosis. From this set of suggested surgical corrections, an optimal spinal surgical correction will ultimately be chosen based on the corresponding determined anatomical parameters measured during simulated walking.

In step 112, iterative simulations are performed to determine a surgical correction from the set that results in acceptable selected lower limb parameters and selected pelvic parameters throughout the gait cycle of the subject. This step may be performed, for example, by measuring the pelvic parameters resulting from a certain suggested spinal surgical correction, adjusting one or more pelvic parameters that are not within acceptable ranges by adjusting anatomical features representing the pelvis in the images. Then a relationship model may be used to relate lower limb parameters to pelvic parameters and to adjust the lower limb parameters respectively in the motion capture images to determine if the lower limb parameters are within an acceptable range throughout the gait cycle.

For the spinal surgical correction which has been deemed acceptable for the lower limb and pelvic parameters, it is then determined, in step 113, if the spinal parameters are within an acceptable range throughout the gait cycle. If the spinal parameters are within an acceptable range throughout the gait cycle, one or more selected relationship models relating any of spinal, pelvic and lower limb parameters to positions of spinal features in the three-dimensional images may be used to output a final spinal surgical correction in step 117.

If the spinal parameters are not within an acceptable range throughout the entire gait cycle, in step 114, spinal parameter optimization, for example SVA optimization, is used on one or more motion capture time sequence images in order to bring all OOR spinal parameters within acceptable ranges throughout the gait cycle of the subject. An advantageous method of spinal parameter optimization is SVA optimization, which is shown in FIG. 11, although other alternative spinal parameters, such as TK or LL in the sagittal plane, may likewise be optimized. The iterative adjustments in the motion capture images as described above may be performed in accordance with the methods of FIGS. 9A and 9B, for example.

In step 115, it is determined if the spinal parameter optimization resulted in pelvic and lower limb parameters within their acceptable ranges throughout the gait cycle of the subject.

If not all pelvic and lower limb parameters are within their acceptable ranges throughout the gait cycle, in step 116, a new surgical correction is chosen from the set of step 111 and it is ensured that this correction results in acceptable lower limb and pelvic parameters throughout the gait cycle of the subject, and the method returns to step 113 to determine if all the spinal parameters are within an acceptable range throughout the gait cycle.

If all pelvic and lower limb parameters are within their acceptable ranges throughout the gait cycle, one or more selected relationship models relating any of spinal, pelvic or lower limb parameters to anatomical features in the three-dimensional images may be used to output an optimal spinal surgical correction. Suitable models are selected for relating any of spinal, pelvic and lower limb anatomical parameters to simulated surgical corrections on three-dimensional images at all phases throughout a simulated gait cycle. From these models it is possible to determine a corresponding surgical correction for the optimized parameters. Such a model may, for example, be able to determine how, for given lower limb and pelvic parameters in a motion capture sequence, spinal anatomy would need to be adjusted in CT images to obtain such parameters, and then to determine what surgical correction would obtain such spinal adjustments in the CT images.

The above described relationship models may be built from three-dimensional and motion capture image data from a single subject, or from multiple subjects. In some cases, data to build these models may be taken from a large database comprising three-dimensional images and motion capture images from a large number of subjects. Artificial intelligence or machine learning may be used to better recognize correlations and to improve the accuracy of these models.

Reference is made to FIGS. 12A, 12B, 12C and 12D, which show an exemplary detailed flowchart of the method of FIG. 10.

Reference is now made to FIG. 12A. In step 120, three dimensional images, for example CT images, are obtained of a subject.

In step 121, a motion capture time sequence of the same subject is obtained. In step 122, each image in the motion capture time sequence is correlated to a phase or subphase in the gait cycle, such as in the examples shown in FIG. 7 and FIG. 8. In step 123, the Global Balance parameters, which generally include spinal, lower limb and pelvic parameters, are measured in each image in the motion capture time sequence. In step 124, it is determined if each Global Balance Parameter is within an acceptable range, given its respective phase or subphase in the gait cycle as determined in step 122.

In step 125, the results of step 124 are used to determine the pathology or diagnosis of the subject and his complete Global Alignment. In step 126, a set of alternative suggested spinal surgical corrections is provided, which each correction being suitable for correcting the pathology or diagnosis determined in step 125. In step 127, a first suggested spinal surgical correction is selected from the set of step 126 to be used in a simulation. Such a first surgical correction may be suggested by the system, by a user or by both, and is generally chosen due to its high likelihood of success for the diagnosis. In step 128, the selected spinal surgical correction is simulated on the CT images. This generally involves adjusting the size, geometry, position, or orientation of spinal anatomical elements on the CT images, for example, fusing two vertebrae, and may also involve implanting non-anatomical elements into the image, such as a wedge. In step 129, a relationship model is used to determine the expected pelvic parameters of the subject throughout the gait cycle resulting from the simulated correction of step 128. In step 130, walking is simulated with the selected surgical correction by adjusting the pelvic parameters in the existing motion capture sequence to those determined in step 129. The lower limb parameters may be adjusted respectively according to a relationship model. It is noted that throughout this method, when a parameter is increased or decreased, certain predefined biomechanical rules of how to adjust the anatomy to achieve such an increase or decrease are followed, for example, those methods discussed in in WO 2017/064719, such as use of an Instantaneous Axis of Rotation (IAR), not adjusting the distance between vertebrae, and adjusting segments rather than individual vertebrae.

Thus, to adjust a typical parameter that consists of three connected anatomical points, two or more segments of anatomy related to these points may be adjusted. In step 131, it is determined if the lower limb parameters resulting from the simulation are within an acceptable range throughout the gait cycle of the subject. If not, a new suggested surgical correction is selected from the set of step 126, and the method returns to step 128. If the lower limb parameters are acceptable throughout the gait cycle, in step 132, the spinal parameters resulting from the simulated correction are determined using a relationship model.

In step 133, it is determined if the spinal parameters are within an acceptable range throughout the gait cycle. If yes, the final surgical correction may be output in step 138. If the spinal parameters are not all within acceptable ranges throughout the gait cycle, in step 135, Out of Range (OOR) spinal parameters are identified and the divergence of each the OOR spinal parameters is determined from the acceptable range.

In step 136, a first pelvic parameter is selected for adjustment. In step 137, the selected pelvic parameter is increased or decreased by an increment within the acceptable range of the pelvic parameter. In step 139, it is determined if all pelvic parameters and spinal parameters are within an acceptable range for the entire gait cycle. If yes, a relationship model may be used to output a final surgical correction.

If not all pelvic and spinal parameters are within an acceptable range for the entire gait cycle, in step 140, it is determined if divergence from the OOR spinal parameters is less. If it is less, in step 141, the increase or decrease performed in step 137 is repeated, and the method proceeds to step 142. If the divergence of the OOR spinal parameters from their acceptable ranges is not less, in step 147, the opposite of the increase or decrease of step 137 is performed, and the method returns to step 139. It is assumed that there is no such thing as divergence from one spinal parameter normal range to decrease while divergence from another spinal parameter normal range increases. The parameters will converge as a skeleton approaches overall optimal global balance and alignment.

In step 142, it is determined if all pelvic parameters and spinal parameters are within an acceptable range for the entire gait cycle. If yes, in step 145, a relationship model may be used to output a final surgical correction. If all the pelvic and spinal parameters are not within acceptable ranges throughout the gait cycle, in step 143, it is determined if all increments of the selected pelvic parameter within acceptable range have been tried. If not, the method returns to step 140. If all the increments within acceptable range have been tried, in step 148, it is determined if all pelvic parameters have been tried. If yes, in step 149, a new surgical correction is chosen from the set of step 126 and the method proceeds to step 128. If not, in step 150, a different alternative pelvic parameter is chosen for adjustment and the method returns to step 137.

Figure 13A:
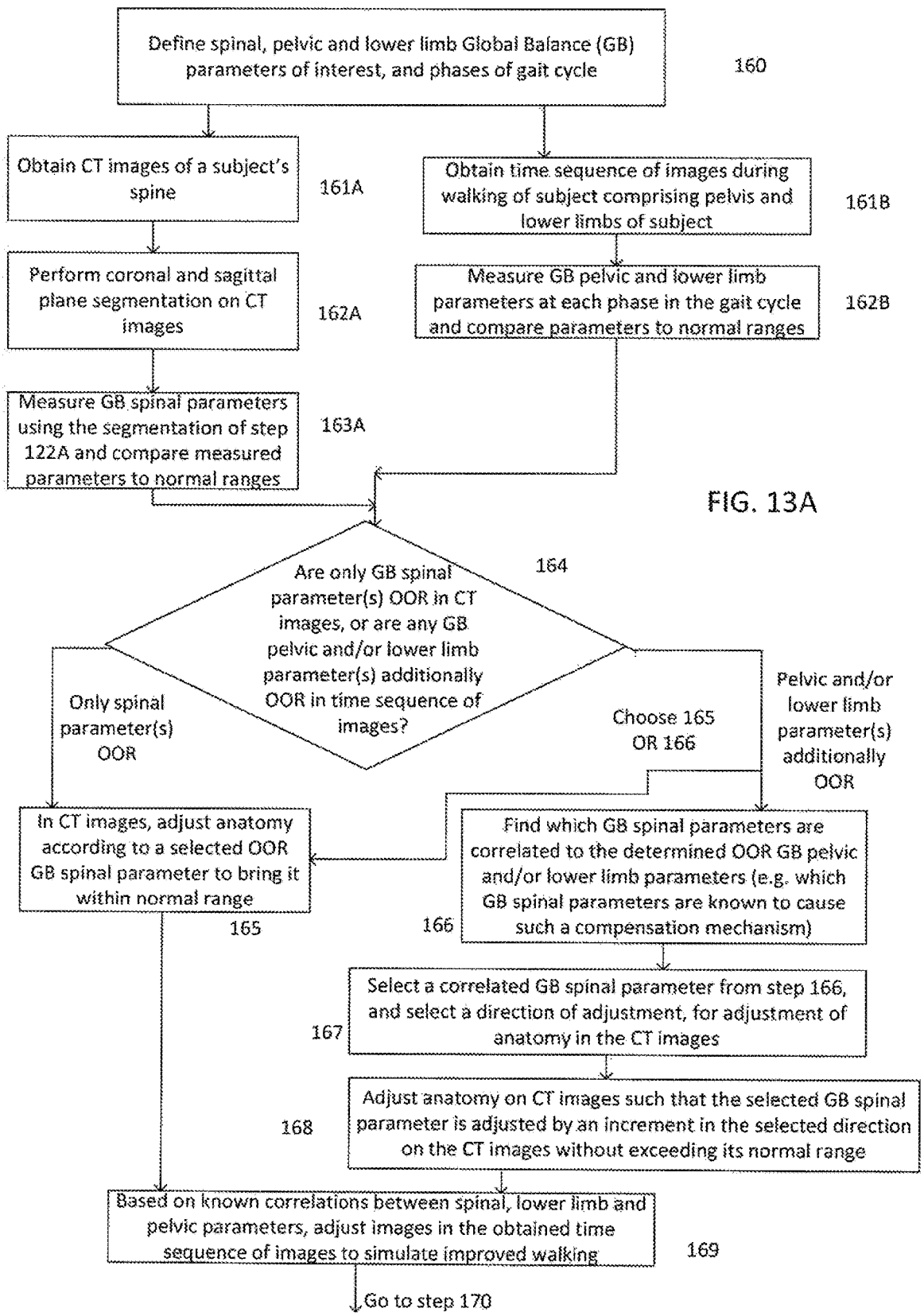
FIGS. 13A and 13B show an exemplary overview flowchart of a method of planning a spinal surgical correction using iterative spinal adjustments of anatomy identified in three-dimensional images of a subject, and observing the effect of the adjustments on dynamic motion images of the subject.
Figure 13B:
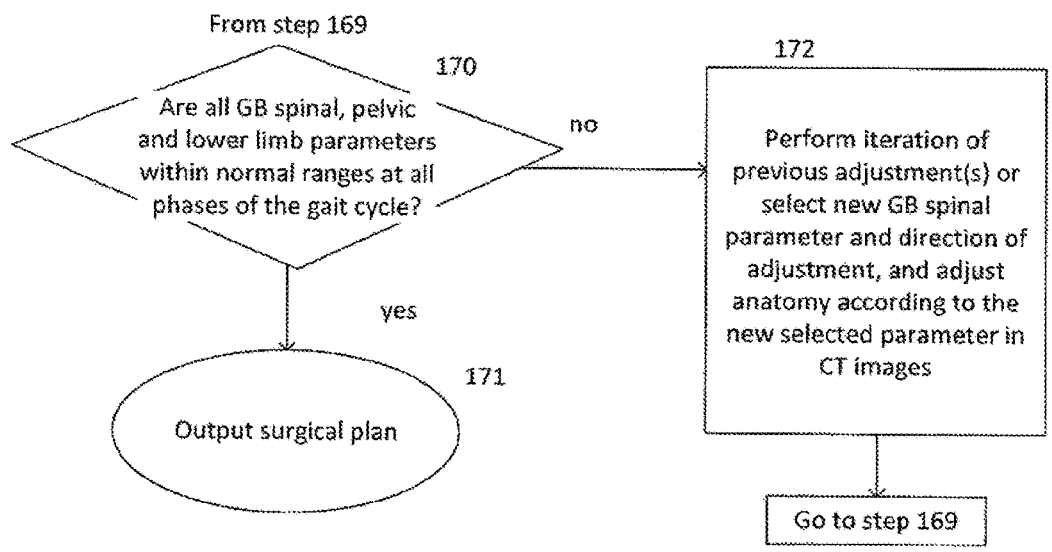

FIGS. 13A and 13B show an exemplary overview flowchart of a method of planning a spinal surgical correction using iterative spinal adjustments in three dimensional images. This method provides an alternative approach to Global Balance parameter optimization by performing iterative adjustments of spinal anatomy in three-dimensional images to bring Out of Range (OOR) spinal, pelvic, or lower limb parameters within range, and then adjusting images accordingly in an obtained time sequence of images to simulate how walking is affected by the adjustments in the three-dimensional images. The time sequence of images may be adjusted accordingly based on known correlations between spinal, lower limb, and pelvic parameters as shown in FIG. 4. In step 130, the spinal, pelvic and lower limb Global Balance parameters of interest are defined, and the phases of the gait cycle are defined. The Global Balance parameters and phases of gait cycle should be defined based on what parameters have clinical relevance in planning spinal surgery, and may be either standard parameters for each patient or may be patient specific parameters, such as those selected based on previously observed compensation mechanisms of a subject. Steps 131A, 132A and 133A, and steps 131B and 132B, may be performed at any time before step 134, and it is irrelevant whether the CT images are obtained before or after the time sequence of images is obtained. In step 131A, CT images of a subject's spine are obtained, for a straightforward example for ease of understanding CT images are obtained of the entire spine. In step 132A coronal and sagittal plane segmentation is performed on the CT images, providing an approximate relative position and orientation of each vertebrae. This step is important both for allowing Global Balance parameters to be measured, including those relating to both the sagittal plane (e.g. Lumbar Lordosis, Thoracic Kyphosis) and coronal planes (e.g. Coronal Balance), and also provides the quantitative data necessary for the adjustment of spinal anatomy in the CT images, as will be discussed later in the method.

In step 133A the Global Balance spinal parameters that have their relevant anatomical reference points in the CT images are measured in the CT images using the segmentation of step 132A, and the measured parameters are compared to normal ranges. A normal range for each spinal parameter may be defined based on a variety of factors, and may be either standard for all patients or patient-specific. Patient-specific spinal parameter normal range may consider such factors as body type, weight height Body Mass Index (BMI), age, ethnicity, and gender. A normal range for each spinal parameter may further be defined in relation to other parameters, for example, as previously described, Pelvic Incidence and Lumbar Lordosis are two intimately connected parameters whose relationship has clinical relevance in spinal surgical planning. In step 131B a time sequence of images is obtained of the subject during walking, comprising at least the pelvis and lower limbs of the subject, and should preferably comprise the entire skeleton including the spine. In step 132B, the Global Balance parameters that have their relevant anatomical reference points in the time sequence of images are measured, for example, the pelvic and lower limb parameters, and are compared to normal ranges. Multiple time sequences may be obtained, and the parameters may be measured in these time sequences, for more accurate analysis.

In step 134, it is determined if only the spinal parameters are Out of Range in the CT images, or if there are additionally other OOR non-spinal anatomical parameters, such as pelvic and lower limb parameters. This method is based on the assumption that any OOR non-spinal parameters are compensation mechanisms due to spinal deformity, and attempts to correct the spine to bring these non-spinal parameters within normal ranges. It is to be understood that the disclosed methods may be used in combination with other spinal or non-spinal surgery planning methods, to consider various other possibilities such as a subject that requires non-spinal surgery in addition to spinal surgery, or a subject that requires spinal surgery regardless of the fact that his spinal parameters appear to be within normal range, or a subject that requires as part of his spinal surgery corrections that are not related to alignment. As one limited example of the latter case, the subject may require decompression for a bulging disc. The disclosed methods may be used in combination with the methods of WO 2017/064719, such as those methods that consider range of motion limitations of the subject.

Figure 1A:
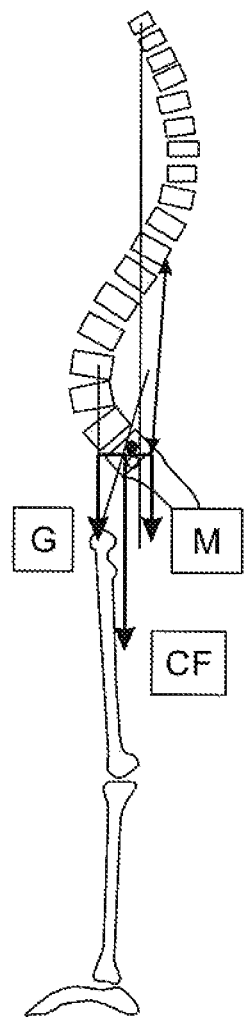
FIGS. 1A, 1B, and 1C are schematic representations showing the effect of alignment of the spine on three forces: Contact Force (CG) on the distal lumber spine, Gravity force (G), and the force M acting on the posterior muscles to maintain an erect position.
Figure 1B:
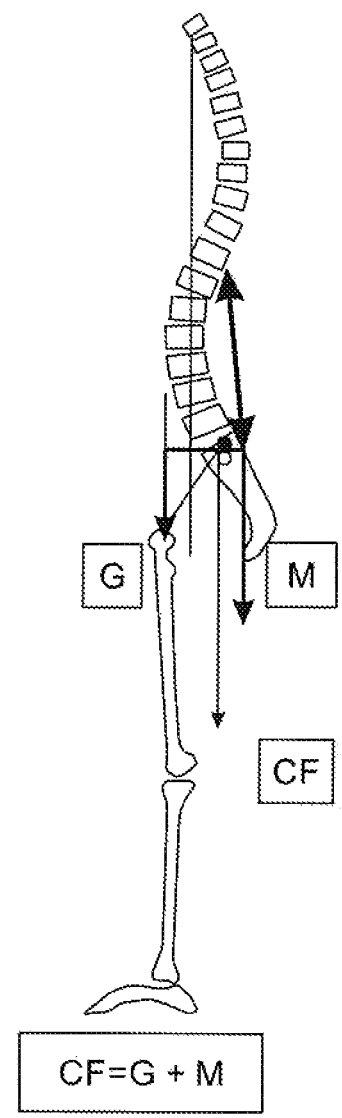
Figure 1C:
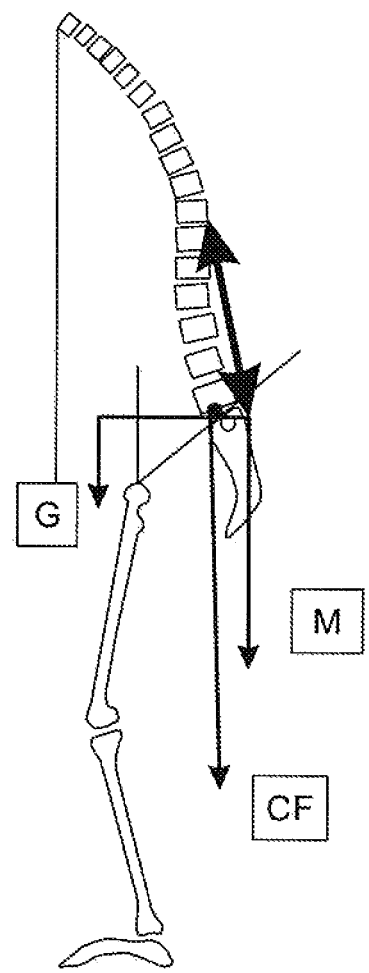
Figure 2:
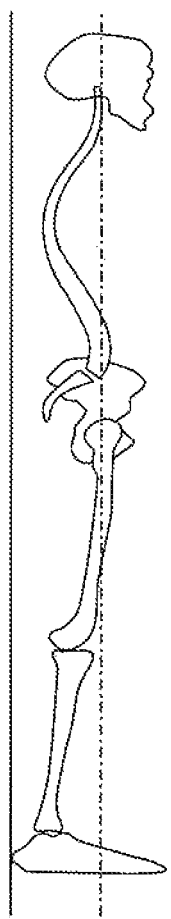
FIG. 2 shows a schematic drawing of a full skeleton with an important Global Balance Parameter, Gravity Line (GL).
Figure 3A:
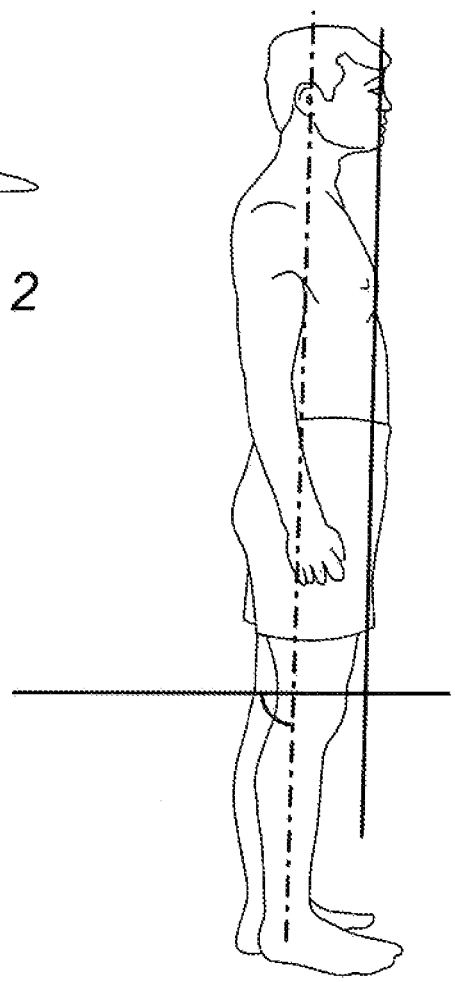
FIG. 3A shows a subject with normal posture.
Figure 3B:
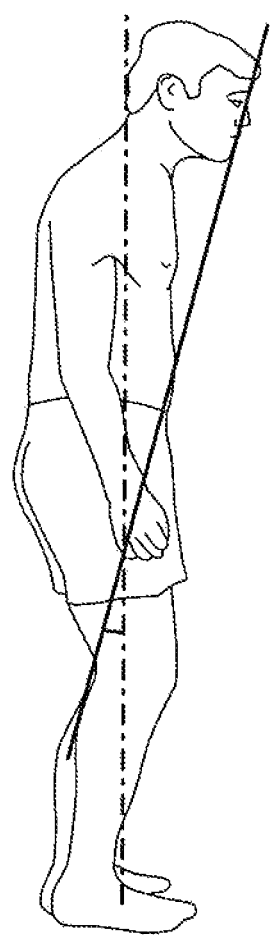
FIG. 3B shows a subject with advanced ankylosing spondylitis, and the respective Chin Brow Vertical Angles (CBVA) of the subject is shown for each.
Figure 4A:
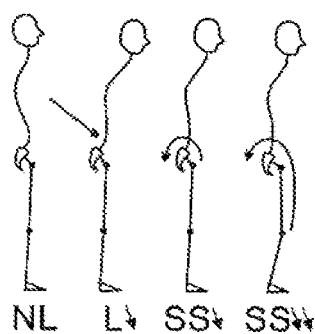
FIGS. 4A, 4B and 4C show three different types of spinal sagittal disturbances and their evolution, including their effect on the pelvis and lower limbs.
Figure 4B:
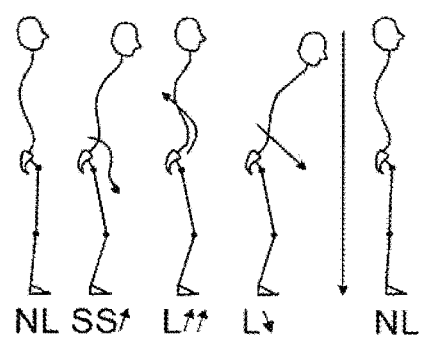
Figure 4C:
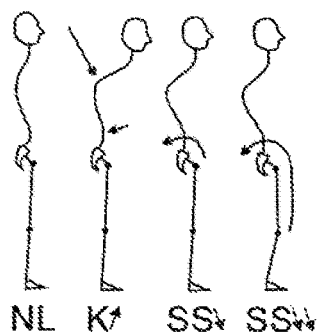
Figure 5:
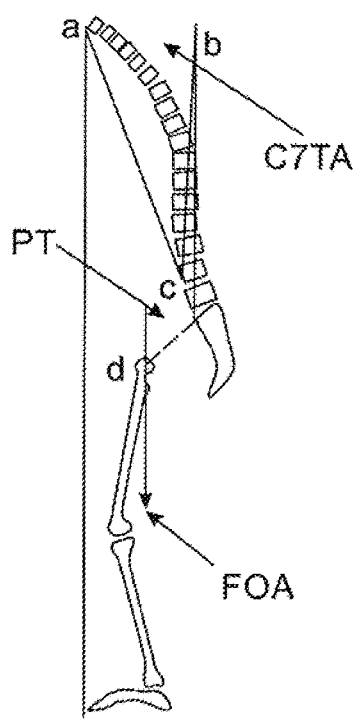
FIG. 5 shows a schematic segmented skeleton with three Global Balance Parameters: C7 Transition Angle (C7TA, Femur Obliquity Angle (FOA), and Pelvic Tilt (PT).

If only one or more spinal parameters are determined to be OOR, and all the non-spinal parameters in the time sequence of images are within normal ranges, then the method proceeds to step 135, where an OOR spinal parameter is selected and anatomy is adjusted in the CT images to bring this OOR spinal parameter within normal range. If it is determined that the subject has both OOR spinal parameters in the CT images, and also OOR pelvic and/or lower limb parameters in the time sequence of images, the method may proceed either to 135 or 136, depending on the best judgement of the system or doctor. Such a decision may be made, for example, based on which parameters are farthest from normal range, since it may be more efficient to adjust these parameters first. If it is decided that an OOR spinal parameter should be adjusted first, before optimizing the lower limbs and pelvis, the method proceeds to step 135. If it is decided that an OOR non-spinal parameter should be optimized first, the method proceeds to 136, where GB spinal parameters are correlated to the determined OOR GB non-spinal parameters, for example the pelvic and lower limb parameters. Such correlations may be determined using a look-up table, for example, comprising the correlations shown in FIGS. 4A to 4C. It is known on a general scale how spinal parameters are correlated to lower limb and pelvic parameters, for example, FIG. 4A shows that when lack of Lordosis (L) with a Sacral Slope (SS) value too low relative to the value of Pelvic Incidence (PI), the pelvic reaction is generally a backward rotation (i.e. retroversion), as shown by the counterclockwise rotational arrows in FIG. 4A, achievable by extension of the hips, and by concomitant flexion of the knees and flexion of the ankles.

Alternatively, such correlations between non-spinal parameters and spinal parameters may be determined based on a doctor's experience and judgment, machine learning or by using Artificial Intelligence. In step 137, a GB spinal parameter is chosen, and a direction of adjustment chosen (i.e. increase or decrease of parameter), based on the correlations of the measured OOR pelvic and lower limb parameters to respective spinal parameters step 136. In step 138, spinal anatomy is adjusted on the CT images such that the selected GB spinal parameter, for example, Lumbar Lordosis, is adjusted by an increment in the selected direction. The spinal parameter must only be adjusted such that it does not exceed its predefined normal range. In step 139, images in the obtained time sequence of images are adjusted to reflect the spinal adjustment of step 135 or 138, according to known correlations between spinal, lower limb and pelvic parameters. For example, a spinal parameter may be increased by increment of X degrees in a first time sequence image, and then a lower limb parameter may be decreased by increment of Y degrees based on a known correlation. This adjustment can then be applied to the other images in the time sequence of images, by increasing the spinal parameter by an increment of X degrees and by decreasing the lower limb parameter by an increment of Y degrees in each of the images. Since each of the images in the time sequence represents a different phase in the gait cycle, the parameters in each of the original obtained time sequence of images are usually different, and thus this approach of "adding" and "subtracting" increments from the pre-existing parameters, takes into account these differences, providing an accurate simulation of how an adjustment will affect the gait cycle of the subject. Such a simulation may be a dynamic visual simulation that may be advantageous for further analysis by a doctor, or the simulation may be purely mathematical data stored in the system, with the system providing an indication whether the parameters are within normal ranges or not. In step 140, it is determined if all GB spinal lower limb and pelvic parameters are within normal ranges at all phases of the gait cycle. This step may be performed simply by calculating the resulting parameters from the one or more adjustments in each image. If all the GB spinal, pelvic and lower limb parameters are within normal ranges at all phases of the gait cycle, the surgical plan, which is generally in the form of CT images, is output in step 141. If the parameters are not all within normal ranges at all phases in the gait cycle, the method proceeds to step 142, where one or more iterations of previous adjustments are performed, or where a new spinal parameters and direction of adjustment is selected and then the anatomy adjusted accordingly on the CT images. Generally, an iteration of a previous adjustment is a repetition of an increase or decrease by the same increment as was previously performed, but if it is observed that the parameters are not moving closer to normal ranges as the iterations are performed, then the iteration may be the opposite of the increase or decrease previously performed.

Likewise, a different size of increment may be chosen for a new iteration, for example, if the parameters are still quite far from normal ranges, a larger increment may be chosen for efficiency in achieving optimization. From step 142, the method returns to step 139 where a simulation is performed of improved walking of the subject. Ultimately, the iterations will result in output of a final surgical plan in step 141, since the spinal, pelvic, and lower limb parameters will converge as a skeleton approaches overall optimal global balance and alignment.

This exemplary flowchart shows three-dimensional images obtained of a subject's spine, and a time sequence of images obtained of a subject's pelvis and lower limbs. It is to be understood that this approach may be used for any three-dimensional imaged and time-sequence-imaged parameters. For example, if only a small segment of the spine is imaged in the three-dimensional images it may be necessary to measure spinal parameters on the time sequence of images and then adjust the small segment according to the required spinal parameter adjustment in the three-dimensional images. As another example, either the time sequence of images or the three-dimensional images may include cranial anatomy, such that GB parameters involving the head, such as CAVA, may be measured and considered in the optimization of anatomy in the three-dimensional images. Furthermore, it is to be understood that although this exemplary flowchart describes a gait cycle, this method may be applied to any type of movement of the subject for which normal or acceptable range GB parameters may be clearly defined, such as spinal flexion or extension. Furthermore, it is to be understood that the term "normal range" is not limited to a clinical definition of health and may in fact be an optimal range or even an optimal value, either being within a normal range. The goal of the optimization is patient specific; thus, for some patients, the goal may be to achieve an optimal range and the method may continue until this optimal range is achieved, while for other patients, it may be impossible to optimize all the spinal, lower limb, and pelvic parameters simultaneously, and thus the goal of the method may be to achieve parameters as close as possible to normal range, such that the final surgical plan output comprises some parameters within normal range, and some close to normal range.

It is to be understood that although in FIGS. 10, 11, and 12A to 12D, a pathology or diagnosis of the subject is determined and then a set of alternative suggested spinal surgical corrections is chosen accordingly, alternative methods of the present disclosure may not use either or both of these steps and may instead commence with optimization of Global Balance spinal, pelvic and/or lower limb parameters, for example as shown in FIGS. 9A and 9B.

Figure 14:
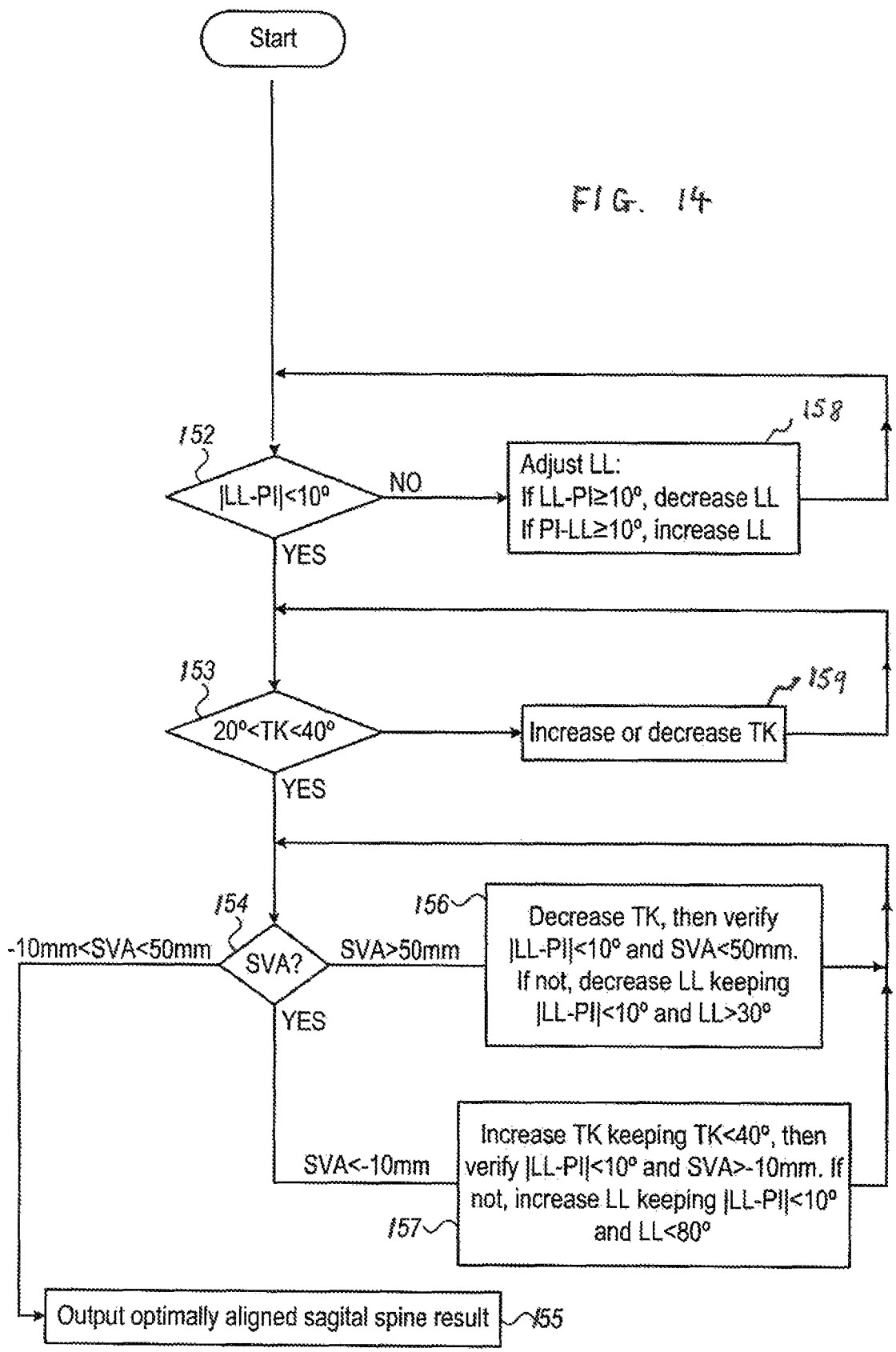
FIG. 14 shows an exemplary detailed flowchart of a spinal parameter optimization method as may be used in the method of FIGS. 11 and 13A to 13B, using Sagittal Vertical Axis (SVA) optimization.

FIG. 14 shows an exemplary method of SVA optimization that may be used, for example, in the method of FIG. 11 or 13A to 13B. This method may be used to optimize the spinal parameters after the lower limb and pelvic parameters have been optimized. In step 150, it is determined if the absolute value of Lumbar Lordosis minus Pelvic Incidence, |LL-PI|, is less than 10 degrees. If it is not, LL must be increased or decreased in step 151. Once |LL-PI| is less than 10 degrees, it is determined in step 152, if Thoracic Kyphosis (TK) is between 20 degrees and 40 degrees. If not, in step 153, Thoracic Kyphosis is increased or decreased until it is within the acceptable range. Once Thoracic Kyphosis is within the acceptable range, it is determined in step 154, if SVA is within the acceptable range of −10 mm to 50 mm. If SVA is greater than 50 mm, in step 155, TK is decreased and then it is verified that |LL-PI|<10 degrees and that SVA is less than 50 mm. If not, LL is decreased keeping |LL-PI|<10 degrees and LL>30 degrees. Once SVA is less than or equal to 50 mm, it is determined if SVA is less than −10 mm. If so, in step 157, TK is increased, keeping TK<40 degrees, and then it is verified that |LL-PI|<10 degrees and SVA>−10 mm. If not, LL is increased keeping |LL-PI|<10 degrees and LL<80 degrees, until SVA falls within the acceptable range of −10 to 50 mm. Once SVA is within the acceptable range, the optimally aligned sagittal spine result is output in step 156, including the corresponding spinal parameters.

While it is to be understood that these exemplary disclosed methods are iterative methods, multiple parameter optimization algorithms may be used to optimize pelvic, spinal and lower limb parameters simultaneously. For example, simulated annealing, particle swarm optimization or genetic algorithms may be used. Additionally or alternatively, such multiple parameter optimization algorithms may be used to optimize one or more pelvic parameters simultaneously, one or more spinal parameters simultaneously, or one or more lower limb parameters simultaneously. Use of such algorithms may provide a faster result, and the accuracy of such algorithms may be assisted by use of supervised or unsupervised machine learning.

It is appreciated by persons skilled in the art that the present disclosure is not limited by what has been particularly shown and described hereinabove. Rather the scope of the present disclosure includes both combinations and subcombinations of various features described hereinabove as well as variations and modifications thereto which would occur to a person of skill in the art upon reading the above description and which are not in the prior art.

We claim:

1. A method of determining a surgical spinal correction for a subject using analysis of a time sequence of a movement progression during motion of said subject, comprising:
   (i) obtaining pre-operative three-dimensional images of a spinal region of a subject;
   (ii) obtaining a pre-operative time sequenced set of images comprising spinal anatomical elements and at least one of pelvic elements or lower limb elements of the subject during a movement progression of said subject;
   (iii) calculating in a plurality of said pre-operative time-sequenced images, selected alignment parameters comprising at least one of a lower limb parameter or a pelvic parameter, and determining if any of said calculated alignment parameters are outside their respective predetermined acceptable ranges in one or more of said pre-operative time-sequenced images;
   (iv) on a selected pre-operative time-sequenced image, adjusting at least one of lower limb or pelvic elements to bring a calculated alignment parameter that is outside of its predetermined acceptable range to within its predetermined acceptable range, and adjusting other relevant spinal anatomical elements that are identifiable in the selected pre-operative time-sequenced accordingly, based on known relationships between spinal and non-spinal anatomical elements;
   (v) adjusting spinal anatomical elements and at least one of pelvic elements or lower limb elements in other images in said pre-operative time sequenced set corresponding to degrees of said adjustments used in step (iv);
   (vi) calculating said selected alignment parameters in said other images, and if any calculated alignment parameters are not within their respective predetermined acceptable ranges, repeating steps (iii) to (v) iteratively until all of said calculated alignment parameters are within their respective predetermined acceptable ranges; and (vii) adjusting spinal anatomy as observed in said pre-operative three-dimensional images according to the degrees of adjustment of said spinal anatomical elements, between those in the obtained pre-operative time sequenced set of images and those in the final iteration of step (vi), to determine a surgical spinal correction for the subject.

2. A method according to claim 1, wherein said calculated alignment parameters further comprise at least one spinal parameter.

3. A method according to claim 2, wherein steps (iv) to (vi) comprise first adjusting pelvic alignment parameters until said pelvic alignment parameters are all within normal ranges, and subsequently adjusting spinal alignment parameters.

4. A method according to claim 2, wherein steps (iv) to (vi) comprise first adjusting spinal alignment parameters until said spinal alignment parameters are all within normal ranges, and subsequently adjusting pelvic alignment parameters.

5. A method according to claim 2, wherein said at least one spinal parameter comprises at least one of cervical, thoracic, lumbar or sacral parameters.

6. A method according to claim 1, wherein said step of adjusting other relevant spinal anatomical elements in the selected pre-operative time-sequenced image based on known relationships between different anatomical elements, reduces or eliminates amendments to anatomical elements representing a lower limb in an image in which said lower limb has reduced weight bearing status.

7. A method according to claim 1, wherein said predetermined acceptable ranges of said alignment parameters are defined for each pre-operative time-sequenced image according to the moment in time of that image during the movement progression of said subject.

8. A method according to claim 1, wherein said movement progression of said subject is either of walking or running, and said predetermined acceptable ranges are defined according to phases in a gait cycle while walking or running.

9. A method according to claim 1, wherein said movement progression of said subject is spinal extension, flexion or rotation.

10. A method according to claim 1, wherein the step of adjusting spinal anatomy in said pre-operative three-dimensional images according to the degrees of adjustment of spinal parameters, is further performed according to at least one of anatomical limitations, biomechanical limitations, or range of motion limitations of said subject.

11. A method according to claim 1, further comprising determining a diagnosis of said subject based on said calculated alignment parameters.

12. A method according to claim 1, wherein said alignment parameters are derived from any type of relations between anatomical elements which are at least one of angular or distance measurements.

13. A method according to claim 1, wherein said alignment parameters comprise at least one of a C7 Translation Angle (C7TA), Thoracic Kyphosis, Lumbar Lordosis, Sagittal Vertical Axis, Hip Knee Ankle, Chin Brow Vertical Angle, Pelvic Incidence—Lumbar Lordosis (PI-LL) mismatch, Cobb angle, Pelvic obliquity, Apical Vertebral Translation—Thoracic (AVT-T), Apical Vertebral Translation—Lumbar AVT-L, Pelvic incidence (PI), Pelvic tilt (PT), Sacral slope (SS) Femoropelvic Angle (FPA), Femoral Tilt Angle (FTA), Femoral Obliquity Angle (FOA), Spinosacral Angle (SSA), Spinopelvic Angle (SPA).

14. A method according to claim 1, wherein said predetermined acceptable ranges of said alignment parameters are further defined according to a body type of said subject.

15. A method according to claim 1, wherein said pre-operative time sequenced set of images is obtained using a motion capture time sequence camera that images markers on said subject indicating said spinal anatomical elements.

16. A method according to claim 1, wherein adjusting other relevant anatomic elements in the selected pre-operative time-sequenced image accordingly in step (iv) is performed using a database comprising known relationships between any of the spinal region, pelvis and lower limbs.

17. A method according to claim 1, wherein step (iv) further comprises adjusting pelvic alignment parameters to bring lower limb alignment parameters within normal ranges.

18. A method according to claim 1, wherein adjusting other relevant spinal anatomical elements in the image accordingly in step (iv) is performed to comply with said previously adjusted spinal anatomical elements.

19. A method according to claim 1, wherein said pre-operative three-dimensional images are any one of CT images, X ray images, or MRI images.

20. A method according to claim 1, wherein said pre-operative three-dimensional images comprise a set of two-dimensional images of said subject.

* * * * *